US012263009B1

(12) United States Patent
Giuffrida et al.

(10) Patent No.: US 12,263,009 B1
(45) Date of Patent: **\*Apr. 1, 2025**

(54) MOVEMENT DISORDER CONTINUOUS MONITORING AND THERAPY SYSTEM

(71) Applicant: Great Lakes NeuroTechnologies Inc., Cleveland, OH (US)

(72) Inventors: Joseph P. Giuffrida, Hinckley, OH (US); Dustin A. Heldman, Shaker Heights, OH (US); Thomas O. Mera, Columbus, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 1246 days.

This patent is subject to a terminal disclaimer.

(21) Appl. No.: 17/001,777

(22) Filed: Aug. 25, 2020

Related U.S. Application Data

(63) Continuation of application No. 15/847,970, filed on Dec. 20, 2017, now Pat. No. 10,786,199, which is a (Continued)

(51) Int. Cl.
*A61B 5/00* (2006.01)
*A61B 5/11* (2006.01)
(Continued)

(52) U.S. Cl.
CPC .......... *A61B 5/4839* (2013.01); *A61B 5/0022* (2013.01); *A61B 5/0024* (2013.01);
(Continued)

(58) Field of Classification Search
CPC ... A61B 5/4839; A61B 5/0024; A61B 5/1101; A61B 5/4082; A61B 5/1723; A61B 5/4836; A61N 1/36067
See application file for complete search history.

(56) References Cited

U.S. PATENT DOCUMENTS 6,440,067 B1 * 8/2002 DeLuca ............... A61B 5/0002
128/920
8,187,209 B1 * 5/2012 Giuffrida ............ A61M 5/1723
600/595

(Continued)

FOREIGN PATENT DOCUMENTS

WO    WO-0047108 A1 * 8/2000 ........... A61B 5/0002

OTHER PUBLICATIONS

"A new actigraph for long-term registration of the duration and intensity of tremor and movement", van Someren, E.J.W., et al., IEEE Transactions in Biomedical Engineering, vol. 4, No. 3, pp. 386-395 (IEEE, Mar. 1998) (Year: 1998).*

*Primary Examiner* — Nathan R Price
*Assistant Examiner* — Adam J. Cermak
(74) *Attorney, Agent, or Firm* — Brian Kolkowski

(57) ABSTRACT

The present invention relates to a movement disorder monitor, and a method of measuring the severity of a subject's movement disorder. The present invention additionally relates to a treatment delivery system for treating a subject in response to changes in the severity of a subject's symptoms. The present invention further provides for a system and method, which can accurately quantify symptoms of movement disorders, utilizing continuously obtained kinetic information to be analyzed, accurately distinguishing between symptoms of movement disorders and activities of daily living, relating quantified symptoms to a standard clinical rating scale, and correlating a subject's symptoms with certain physiological and environmental factors. The present invention still further provides for home monitoring of symptoms in subjects with these movement disorders in order to capture the complex fluctuation patterns of the disease over the course of days, weeks, months, or years.

20 Claims, 23 Drawing Sheets

Related U.S. Application Data continuation of application No. 15/043,779, filed on Feb. 15, 2016, now Pat. No. 9,877,680, which is a continuation of application No. 14/192,990, filed on Feb. 28, 2014, now Pat. No. 9,302,046, which is a continuation of application No. 13/185,302, filed on Jul. 18, 2011, now Pat. No. 8,702,629, which is a continuation-in-part of application No. 11/082,668, filed on Mar. 17, 2005, now Pat. No. 8,187,209.

(51) Int. Cl.
    *A61B 5/389*     (2021.01)
    *A61M 5/172*     (2006.01)
    *A61N 1/36*     (2006.01)
    *A61N 1/372*     (2006.01)

(52) U.S. Cl.
    CPC ............ *A61B 5/1101* (2013.01); *A61B 5/389* (2021.01); *A61B 5/4082* (2013.01); *A61B 5/6824* (2013.01); *A61B 5/6826* (2013.01); *A61M 5/1723* (2013.01); *A61N 1/36067* (2013.01); *A61N 1/36139* (2013.01); *A61N 1/37282* (2013.01); *A61B 5/1123* (2013.01); *A61B 5/4836* (2013.01); *A61B 5/7225* (2013.01); *A61B 5/7264* (2013.01); *A61B 5/7267* (2013.01); *A61B 2562/0219* (2013.01)

(56) References Cited

U.S. PATENT DOCUMENTS

| | | | | |
|---|---|---|---|---|
| 8,583,238 B1* | 11/2013 | Heldman | ............. | A61N 1/0492 607/45 |
| 8,679,038 B1* | 3/2014 | Giuffrida | ............. | A61B 5/4839 600/595 |
| 8,702,629 B2* | 4/2014 | Giuffrida | ............... | A61B 5/389 600/595 |
| 8,845,557 B1* | 9/2014 | Giuffrida | ............. | A61B 5/4839 600/595 |
| 8,928,484 B2* | 1/2015 | Chang | ................... | A61B 5/0002 340/573.7 |
| 9,149,229 B1* | 10/2015 | Tarler | ..................... | A61B 5/398 |
| 9,211,417 B2* | 12/2015 | Heldman | ........... | A61N 1/37235 |
| 9,238,142 B2* | 1/2016 | Heldman | ............. | A61B 5/1124 |
| 9,282,928 B1* | 3/2016 | Giffrida | ............. | A61B 5/6826 |
| 9,289,603 B1* | 3/2016 | Giuffrida | ........... | A61N 1/36067 |
| 9,302,046 B1* | 4/2016 | Giuffrida | .............. | A61B 5/1101 |
| 9,314,190 B1* | 4/2016 | Giuffrida | ........... | A61N 1/36003 |
| 9,662,502 B2* | 5/2017 | Giuffrida | ........... | A61N 1/36135 |
| 9,696,228 B1* | 7/2017 | Tarler | ..................... | A61B 5/112 |
| 9,782,122 B1* | 10/2017 | Pulliam | ................ | A61B 5/4839 |
| 9,877,679 B1* | 1/2018 | Giuffrida | ............. | A61B 5/1123 |
| 9,877,680 B1* | 1/2018 | Giuffrida | ........... | A61N 1/36067 |
| 9,974,478 B1* | 5/2018 | Brokaw | ............. | A61B 5/486 |
| 10,022,545 B1* | 7/2018 | Giuffrida | ............... | A61B 5/389 |
| 10,625,074 B2* | 4/2020 | Rosenbluth | ........ | A61N 1/36034 |
| 10,694,992 B1* | 6/2020 | Giuffrida | ............. | A61B 5/0022 |
| 10,750,946 B1* | 8/2020 | Giuffrida | ............. | A61B 5/742 |
| 10,758,732 B1* | 9/2020 | Heldman | ........... | A61N 1/37235 |
| 10,786,199 B1* | 9/2020 | Giuffrida | ............... | A61B 5/389 |
| 10,786,200 B1* | 9/2020 | Giuffrida | ............. | A61B 5/4082 |
| 10,786,625 B1* | 9/2020 | Giuffrida | ............. | A61B 5/1101 |
| 10,966,652 B1* | 4/2021 | Giuffrida | ............. | G16H 20/10 |
| 11,040,203 B1* | 6/2021 | Giuffrida | ............. | A61B 5/7264 |
| 11,191,968 B1* | 12/2021 | Giuffrida | ........... | A61N 1/37247 |
| 11,363,982 B1* | 6/2022 | Giuffrida | ............. | A61B 5/0022 |
| 11,367,519 B1* | 6/2022 | Heldman | ............. | A61M 5/142 |
| 11,559,250 B1* | 1/2023 | Giuffrida | ............. | A61B 5/1123 |
| 11,786,730 B1* | 10/2023 | Heldman | ........... | A61N 1/37247 607/45 |
| 11,786,735 B1* | 10/2023 | Heldman | ........... | A61N 1/36135 705/2 |
| 11,951,355 B2* | 4/2024 | Fung | ................. | A63B 22/0292 |
| 2003/0050548 A1* | 3/2003 | Schmidt | ................ | A61B 5/325 600/373 |
| 2004/0092809 A1* | 5/2004 | DeCharms | .......... | A61B 5/0048 600/410 |
| 2004/0249422 A1* | 12/2004 | Gliner | .................. | A61N 1/0534 607/45 |
| 2005/0234309 A1* | 10/2005 | Klapper | ............... | A61B 5/6828 600/300 |
| 2006/0015153 A1* | 1/2006 | Gliner | ................ | A61N 1/36135 607/45 |
| 2009/0137565 A1* | 5/2009 | Frucht | .................... | A61K 31/19 514/270 |
| 2010/0030119 A1* | 2/2010 | McNames | ........... | A61B 5/4082 600/595 |

\* cited by examiner

MOVEMENT DISORDER CONTINUOUS MONITORING AND THERAPY SYSTEM

CROSS-REFERENCE TO RELATED APPLICATIONS

This application is a continuation of U.S. patent application Ser. No. 15/847,970, filed on Dec. 20, 2017, issued as U.S. Pat. No. 10,786,199 on Sep. 29, 2020, and which was a continuation of U.S. patent application Ser. No. 15/043,779, filed on Feb. 15, 2016, which issued as U.S. Pat. No. 9,877,680 on Jan. 30, 2018 and which was a continuation of U.S. patent application Ser. No. 14/192,990, filed on Feb. 28, 2014 and issued as U.S. Pat. No. 9,302,046 on Apr. 5, 2016, which was a continuation of U.S. patent application Ser. No. 13/185,302, filed on Jul. 18, 2011, and which issued as U.S. Pat. No. 8,702,629 on Apr. 22, 2014, which was a continuation-in-part of the U.S. patent application Ser. No. 11/082,668, filed Mar. 17, 2005, and which issued as U.S. Pat. No. 8,187,209 on May 29, 2012. The disclosure and drawings of each of the above patents and applications are hereby incorporated by reference in their entirety.

STATEMENT REGARDING FEDERALLY-SPONSORED RESEARCH OR DEVELOPMENT

The U.S. Government has a paid-up license in this invention and the right in limited circumstances to require the patent owner to license others on reasonable terms provided for by the terms of grant numbers 1R43NS043816, 2R44NS043816, and 1R43AG0347081 awarded by the National Institutes of Health.

BACKGROUND OF THE INVENTION

1. Field of the Invention

The present invention relates to a movement disorder monitor, and a method of measuring the severity of a subject's movement disorder. More particularly, it preferably relates to a monitor and method for the continuous monitoring of a movement disorder. The present invention further, optionally, uses the monitor and method of the present invention to titrate or adjust a treatment delivery system including the delivery of drugs or electrical stimulation for treating or dosing a subject in response to changes in the severity of a subject's symptoms. The device and method disclosed herein further relate to monitoring symptoms of movement disorders, such as those associated with Parkinson's disease (PD), essential tremor, dystonia, and Tourette's syndrome, including tremor, bradykinesia, rigidity, gait/balance disturbances, and dyskinesia. Because essential tremor and PD are two of the most prevalent and life-altering types of movement disorders, essential tremor and PD will be the central examples used in describing the present invention. However, the device and method disclosed herein are equally adaptable for use in monitoring and assessing symptoms of any of the movement disorders mentioned herein or any other movement disorder that involves an inability to control movement of the body's extremities.

2. Technology Review

Parkinson's disease is characterized by unnatural motor movements. Most frequently these symptoms are manifested in the form of tremor, bradykinesia and/or rigidity of a subject's upper extremities. However, other symptoms associated with PD include negative effects on gait, balance, speech, olfaction, sleep and cognition. These symptoms are partly responsible for the subject's functional disability and social embarrassment. Various treatments have been developed to alleviate many of the symptoms of PD. The treatments can involve pharmaceutical interventions, fetal cell transplants, surgery, or electrical stimulation, such as deep brain stimulation (DBS) or functional electrical stimulation (FES), in some of these disorders. The efficacy of these interventions is often judged by the interventions' ability to alleviate patient symptoms and improve their quality of life. Furthermore, the efficacy of these interventions often varies greatly throughout the course of a single day, and throughout the course of treatment.

Tremors are one of the most common symptoms associated with movement disorders. They are involuntary muscle contractions characterized by oscillations of a body part. Tremor of the hands can be cosmetically upsetting and affect functional tasks such as grasping of objects. Resting tremors usually occur at frequencies of approximately 4-7 Hz while the frequency of action of postural tremors is higher, usually between 9-11 Hz. Tremor is a symptom often targeted by treatment. The standard clinical method for analyzing rest and postural or action tremor is qualitative assessment by a clinician and assignment of a score.

Bradykinesia refers to delays or hesitations in initiating movements and slowness in executing movements. The standard clinical method for analyzing bradykinesia is qualitative assessment by a clinician and assignment of a score. This score is assigned while the subject completes a repetitive finger-tapping task, a repetitive hand opening-closing task, and a pronation-supination task. Objective assessment by this means is difficult and variable. It has been found that movement rate and time are useful in better characterizing bradykinesia.

Rigidity occurs because muscles of the body are overly excited. The neurons involved in inhibition circuitry have died due to Parkinson's disease and muscles may receive continuous excitation. Rigidity causes the joints of the subject to become stiff and decreases range of motion. During normal movement, an agonist muscle contracts while the antagonist muscles relax. However, due to the constant motor unit input, the antagonist is unable to relax. Again, the standard clinical method for analyzing rigidity is qualitative assessment by a clinician and assignment of a score. To do so a clinician passively moves the subject's joints through a range of motion while the subject relaxes.

Dyskinesias are also one of the most common and disabling complications of chronic drug therapy. Dyskinesias are wild involuntary movements that typically occur when the benefit from the drug therapy is at its maximum. Clinical assessment of dyskinesias typically relies on self-reporting by the subject. There is a great need to objectively quantify these involuntary movements in view of the growing number of pharmacologic agents and surgical procedures to improve dyskinesia.

Gait and balance disturbances are also one of the more severe symptoms of movement disorders. In addition to the obvious effects on a subject's daily living such as mobility and independence, gait and balance disturbances may also lead to falls and additional physical and emotional trauma for suffering subjects. Such disturbances are also subject to a great deal of variance throughout the course of a single day, even while treated, making them difficult to control without a detailed understanding of each individual's disorder.

Standard clinical evaluation involves qualitative assessment of these symptoms. The current standard in evaluating the severity of movement disorder symptoms in Parkinson's disease is the Unified Parkinson's Disease Rating Scale (UPDRS) used to score motor tests, many of which involve repetitive movement tasks such as touching the nose and drawing the hand away repeatedly, or rapidly tapping the fingers together. A battery of exercises, typically a subset of the upper extremity motor section of the UPDRS, is normally completed during sessions to evaluate medication and DBS efficacy, while a clinician qualitatively assesses symptoms. Each test is evaluated by a clinician based solely on subjective visual observation and graded on a scale that ranges from 0 (normal) to 4 (severe). Like the UPDRS, the Tremor Research Group Essential Tremor Rating Assessment Scale (TETRAS), Washington Heights-Inwood Genetic Study of Essential Tremor (WHIGET) tremor rating scale, and Fahn-Tolosa-Marin tremor rating scale (TRS) are also used to evaluate essential tremor on a 0-4 scale.

In an effort to make these ratings more objective, recently some efforts have been made to quantify symptoms of movement disorders. Accelerometers and gyroscopes have been used individually to quantify some of these movement disorder symptoms, however, alone each sensor has limitations. Accelerometers operate in response to the local gravitational field; therefore they often have problems in separating changes in linear acceleration from rotation. Further, results of a second integration required to obtain linear position are often contaminated with noise, making measurement difficult at best. Gyroscopes measure angular velocity independent of gravity with a good frequency response; however, static angular position cannot be measured accurately due to DC drift characteristic with these devices. Combining the information from both accelerometers and gyroscopes can provide a more accurate method of quantifying motion.

Currently, many systems are tethered or bulky, which reduces patient safety, limits home monitoring capabilities, and does not allow for recording of some movement disorder symptoms. Additionally, none of the current systems have software to distinguish symptoms such as tremor and dyskinesia from activities of daily living (ADL), and relate them to standard rating scales such as the UPDRS or TRS. Finally, none of these systems have clinical video instruction or real-time clinical video feedback during continuous monitoring of movement disorders. In all of the treatment methods listed above, it is clear that improved outcomes and management of movement disorder symptoms could be achieved if a clinician were able to obtain objective data on a subject's symptoms beyond that which could be observed in the relatively short time period during which a subject sees a physician or other clinician during a standard office visit.

Accordingly, it is an object of the present invention to provide a device and method for accurately quantifying symptoms of movement disorders. It is still another object of the present invention to provide a system, which accurately quantifies symptoms utilizing both kinetic information and electromyography (EMG) data. It is further an object of the present invention to provide a wireless movement disorder system that can be worn continuously to provide continuous information to be analyzed as needed by the clinician. It is still further another object of the present invention to provide a movement disorder system that can provide analysis in real-time. It is still further another object of the present invention to provide a movement disorder system to allow for home monitoring of symptoms in subject's with these movement disorders to capture the complex fluctuation patterns of the disease over the course of days, weeks, months, or years. It is still further another object of the present invention to correlate a subject's symptoms with certain physiological, environmental and other factors, as well as the subject's assessment of his or her symptoms. It is still further another object of the present invention to distinguish between movement disorder symptoms and activities of daily living based at least in part on the quantitative recorded movement data. It is still further another object of the present invention to maximize subject safety. It is still further an object of the present invention to provide a system with clinical video instruction and real-time clinical video feedback. It is still further an object of the present invention to provide a treatment delivery system that can monitor symptoms in subject's and deliver treatment in response to those symptoms. Finally it is the object of the present invention to provide remote access between the clinician and subject.

SUMMARY OF THE INVENTION

The present invention relates to a movement disorder monitor, and a method of measuring the severity of a subject's movement disorder. The present invention additionally relates to a treatment delivery system including electrical stimulation and/or drugs for treating or dosing a subject in response to changes in the severity of a subject's symptoms. The present invention further provides for a system and method, which can accurately quantify symptoms of movement disorders, utilizing continuously obtained kinetic information from accelerometers and/or gyroscopes, and optionally from electromyography (EMG) data. The present invention still further provides for a system and method for providing continuous information to be analyzed as needed by the clinician, accurately distinguishing between symptoms of movement disorders and activities of daily living, relating quantified symptoms to a standard clinical rating scale, and correlating a subject's symptoms with certain physiological, environmental and other factors, such as the subject's assessment of his or her symptoms. The present invention still further provides for home monitoring of symptoms in subjects with movement disorders in order to capture the complex fluctuation patterns of the disease over the course of days, weeks, months, or years, to further maximize subject safety and provide remote access between the clinician and subject.

A number of embodiments of the present invention are envisioned in this disclosure. The following embodiments are examples of the many embodiments encompassed by the present invention, but do not in any way limit the many other embodiments covered by this disclosure.

In one embodiment, the present invention includes a portable movement disorder device for measuring severity of a subject's movement disorder comprising a first sensor for measuring a subject's external body motion having a signal related to the external body motion; and a second sensor for measuring a subject's electrical muscle activity wherein the severity of the subject's movement disorder is calculated based in part on the signals of the first and second sensors.

In another embodiment, the present invention includes a method of measuring severity of a subject's movement disorder comprising the steps of measuring a subject's external body motion; transmitting wirelessly a signal based in part on the subject's measured external body motion; receiving the wirelessly transmitted signal; and scoring the severity of a subject's movement disorder based in part on the wirelessly transmitted signal.

In still another embodiment, the present invention includes a portable movement disorder device or system for measuring severity of a subject's movement disorder comprising at least one sensor having a signal for measuring a subject's external body motion or physiological signal associated with a movement disorder; at least one processor for receiving the signal, and calculating the severity of the subject's movement disorder in real time.

In still another embodiment, the present invention includes a portable movement disorder device or system for measuring severity of a subject's movement disorder comprising at least one sensor having a signal for measuring a subject's external body motion or physiological signal associated with a movement disorder; recording that data to memory on the device, downloading that data to a computer at a later time and calculating the severity of the subject's movement disorder.

In still another embodiment, the present invention includes a drug delivery system comprising at least one sensor having a signal for measuring a subject's external body motion or physiological signal associated with a movement disorder; an actuator which allows a medication to be delivered from a reservoir external to the subject to a point internal to the subject; and a closed-loop control system for activating and deactivating the actuator based in part on the signal from the at least one sensor.

In still another embodiment, the present invention includes a system for quantifying symptoms of a subject having a movement disorder comprising: a movement measuring apparatus for acquiring movement data corresponding to movement of a subject comprising at least one sensor; a processor in communication with the movement measuring apparatus capable of using a trained algorithm to calculate a score correlated at least in part to a clinician's standardized movement assessment rating score; and a device for outputting or otherwise communicating the score calculated by the trained algorithm to a clinician or other user for review and analysis, wherein the trained algorithm has been trained to distinguish at least in part between voluntary and involuntary movement, and between postural and kinetic tremor.

In still another embodiment, the present invention includes a system for quantifying tremor during activities of daily living in the home, comprising: a movement measuring apparatus for continuously acquiring movement data corresponding to continuous movement of a subject and comprising at least one sensor; a processor in communication with the movement measuring apparatus capable of using a trained algorithm to calculate a score correlated at least in part to a clinician's standardized rating score; and a device for outputting or otherwise communicating the score calculated by the trained algorithm to a clinician or other user for review and analysis, wherein the trained algorithm has been trained to distinguish at least in part between voluntary and involuntary movement, and between postural and kinetic tremor.

In still another embodiment, the present invention includes a method for quantifying tremor during activities of daily living in the home, comprising the steps of: providing a movement measuring apparatus comprising at least one sensor; acquiring movement data continuously from a subject wearing the movement measuring apparatus, the movement data corresponding to continuous movement of the subject; transmitting the movement data from the movement measuring apparatus to a processor; processing, with the processor, the movement data using a trained algorithm to calculate a score that correlates to a clinician's standardized rating score; and outputting the score calculated by the trained algorithm to a clinical device or user for review and analysis, wherein the trained algorithm has been trained to distinguish at least in part between voluntary and involuntary movement, and between postural and kinetic tremor.

In still another embodiment, the present invention includes a system for quantifying symptoms of a subject having a movement disorder comprising: a movement measuring apparatus for acquiring movement data corresponding to movement of a subject comprising at least one sensor; a trained algorithm for distinguishing at least in part between voluntary and involuntary movement, and between postural and kinetic tremor; a processor in communication with the movement measuring apparatus capable of using the trained algorithm to calculate a score correlated at least in part to a clinician's standardized rating score; and a device for outputting or otherwise communicating the score calculated by the trained algorithm to a clinician or other user for review and analysis.

In still another embodiment, the present invention includes a system for quantifying tremor during activities of daily living in the home, comprising: a movement measuring apparatus for continuously acquiring movement data corresponding to continuous movement of a subject comprising at least one sensor; a trained algorithm for distinguishing at least in part between voluntary and involuntary movement, and between postural and kinetic tremor; a processor in communication with the movement measuring apparatus capable of using the trained algorithm to calculate a score correlated at least in part to a clinician's standardized rating score; and a device for outputting or otherwise communicating the score calculated by the trained algorithm to a clinician or other user for review and analysis.

In still another embodiment, the present invention includes a method for quantifying symptoms of a subject having a movement disorder comprising the steps of: providing a movement measuring apparatus comprising at least one sensor; acquiring movement data from a subject wearing the movement measuring apparatus, the movement data corresponding to movement of the subject; transmitting the movement data from the movement measuring apparatus to a processor; training an algorithm to distinguish at least in part between voluntary and involuntary movement, and between postural and kinetic tremor; processing, with the processor, the movement data using the trained algorithm to calculate a score that correlates to a clinician's standardized rating score; and outputting the score calculated by the trained algorithm to a clinician or other user for review and analysis.

In still another embodiment, the present invention includes a method for quantifying tremor during activities of daily living in the home, comprising the steps of: providing a movement measuring apparatus comprising at least one sensor; acquiring movement data continuously from a subject wearing the movement measuring apparatus, the movement data corresponding to continuous movement of the subject; transmitting the movement data from the movement measuring apparatus to a processor; training an algorithm to distinguish at least in part between voluntary and involuntary movement, and between postural and kinetic tremor; processing, with the processor, the movement data using the trained algorithm to calculate a score that correlates to a clinician's standardized rating score; and outputting the score calculated by the trained algorithm to a clinician or other user for review and analysis.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

DESCRIPTION OF THE PREFERRED EMBODIMENT

Figure 1A:
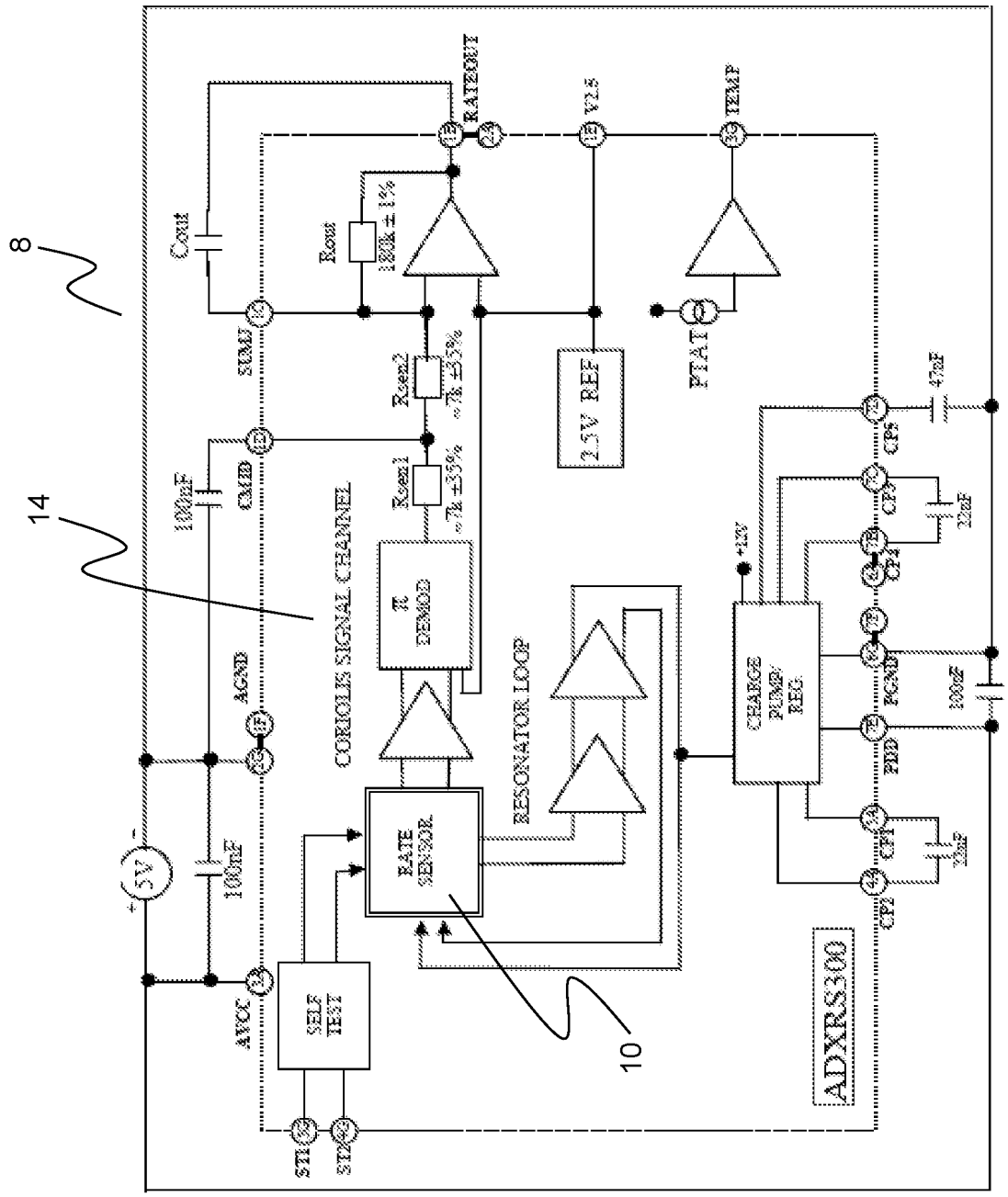
FIGS. 1A-C. Electrical schematics of gyroscopes useful in the present invention: A) and B) are schematics of single-axis gyroscopes; and C) dual-axis gyroscope.

The present invention relates to a movement disorder monitor, and a method of measuring the severity of a subject's movement disorder. The present invention additionally relates to a treatment delivery system including electrical stimulation and/or drugs for treating or dosing a subject in response to changes in the severity of a subject's symptoms.

The devices, systems and methods of the various embodiments of the present invention are used to analyze, score, and treat various movement disorders. Movement disorders for purposes of this application include but are not limited to Parkinson's disease (PD) and essential tremor. Some of the treatments used for these disorders involve pharmaceutical interventions, fetal cell transplants, surgery, or electrical stimulation, such as deep brain stimulation (DBS) or functional electrical stimulation (FES). The efficacy of these interventions is often judged by the interventions' ability to alleviate patient symptoms and improve their quality of life. Furthermore, the efficacy of these interventions often varies greatly throughout the course of a single day, and throughout the course of treatment. The subject on which the devices, system or method is used is a human or other form of animal.

The devices of the various embodiments of the present invention are preferably portable. By portable it is meant among other things that the device is capable of being transported relatively easily. Further, it is relatively easy for the device to be carried by a single person, generally in a carrying case to the point of use or application. Furthermore the device preferably should be relatively light-weight. By relatively light-weight, preferably the device weighs less than about 3 lbs., more preferably less than about 2 lbs., even more preferably less than about 1 lb., even more preferably less than about 0.5 lbs., still more preferably less than about 0.1 lbs., and most preferably less than about 20 grams. By being light-weight and further compact, the device should gain greater acceptance for use by the subject. The system for measuring and calculating the severity of the symptoms including external computers preferably weighs less than about 15 lbs., more preferably less than about 10 lbs., even more preferably less than about 5 lbs., still more preferably less than about 2 lbs., still even more preferably less than about 1 lb., and most preferably less than about 0.5 lbs. This system more preferably can fit in a reasonably sized carrying case so the patient or their caregiver can easily transport the system.

Another advantage of the system(s) and method(s) of the present invention is the ability to determine or calculate the severity of a subject's symptoms in real time. By real time it is meant that within 30 minutes the severity of a subject's symptoms can be calculated or determined. Preferably, the subject's symptoms can be calculated or determined in less than about 30 seconds, more preferably in less than about 1 second, even more preferably in less than about 0.1 seconds, even more preferably in less than about 0.01 seconds, and most preferably in less than about 1 microsecond.

Another advantage of the systems and methods of the present invention is the ability to distinguish the subject's symptoms from activities of daily living during analysis of the recorded movement data. Such symptoms may include tremor, bradykinesia, rigidity, gait/balance disturbances, and dyskinesias. Activities of daily living may include, but are not limited to, folding laundry, handwriting, eating, dressing, self-care, and the like. Such activities are routine tasks not otherwise defined as a test task by one of the standardized rating assessment scales like the UPDRS or TRS. When movement data is continuously collected from a subject for extended periods of time and away from a clinician's office, such as during activities of daily living, recorded movement will be both voluntary and involuntary. Sometimes voluntary and involuntary motion can occur at the same time, such as when a subject suffering from tremor voluntarily moves his hand. Preferably, the system and method of the present invention can use the continually recorded movement data to distinguish voluntary and involuntary motion, as well as determine what activities or tasks were performed. Preferably, by distinguishing motion resulting solely from activities of daily living and motion resulting from disorder symptoms, analysis of the movement data can better quantify the severity of the subject's symptoms. Even more preferably, this analysis can be done in real-time, so as to alert a clinician to any recorded changes in a subject's symptoms and/or automatically tune a treatment delivery device while continuing to record activities of daily living.

The devices of the various embodiments of the present invention can form part of a system for use by a physician, veterinarian, technician or clinician for analysis or evaluation of a subject's movement disorder; for pharmaceutical research; or for delivery of pharmaceutical compounds. Other elements of this system may include but are not limited to receivers, routers, communication devices, processors, displays, drug delivery devices, electrical stimulators (both external and internal), databases, algorithms, and the like, some of which are described further in various embodiments described in more detail below.

Various embodiments of the present invention may include a sensor for measuring a subject's external body motion. Many types of sensors are known by those skilled in the art for measuring external body motion. These sensors include but are not limited to accelerometers, gyroscopes, magnometers, resistive bend sensors, load cells, combinations thereof, and the like. The part of the body wearing the sensor and being measured for motion may be a limb (as at a wrist, ankle, heel, thigh, or finger) or may be the trunk of the body (as at a shoulder, waist, or torso) or according to other techniques known to those skilled in the art. In most embodiments, a combination using at least three axes each of an accelerometer and gyroscope (either as individual or multiple devices) is preferably used at a combination of limb and trunk locations.

Figure 1B:
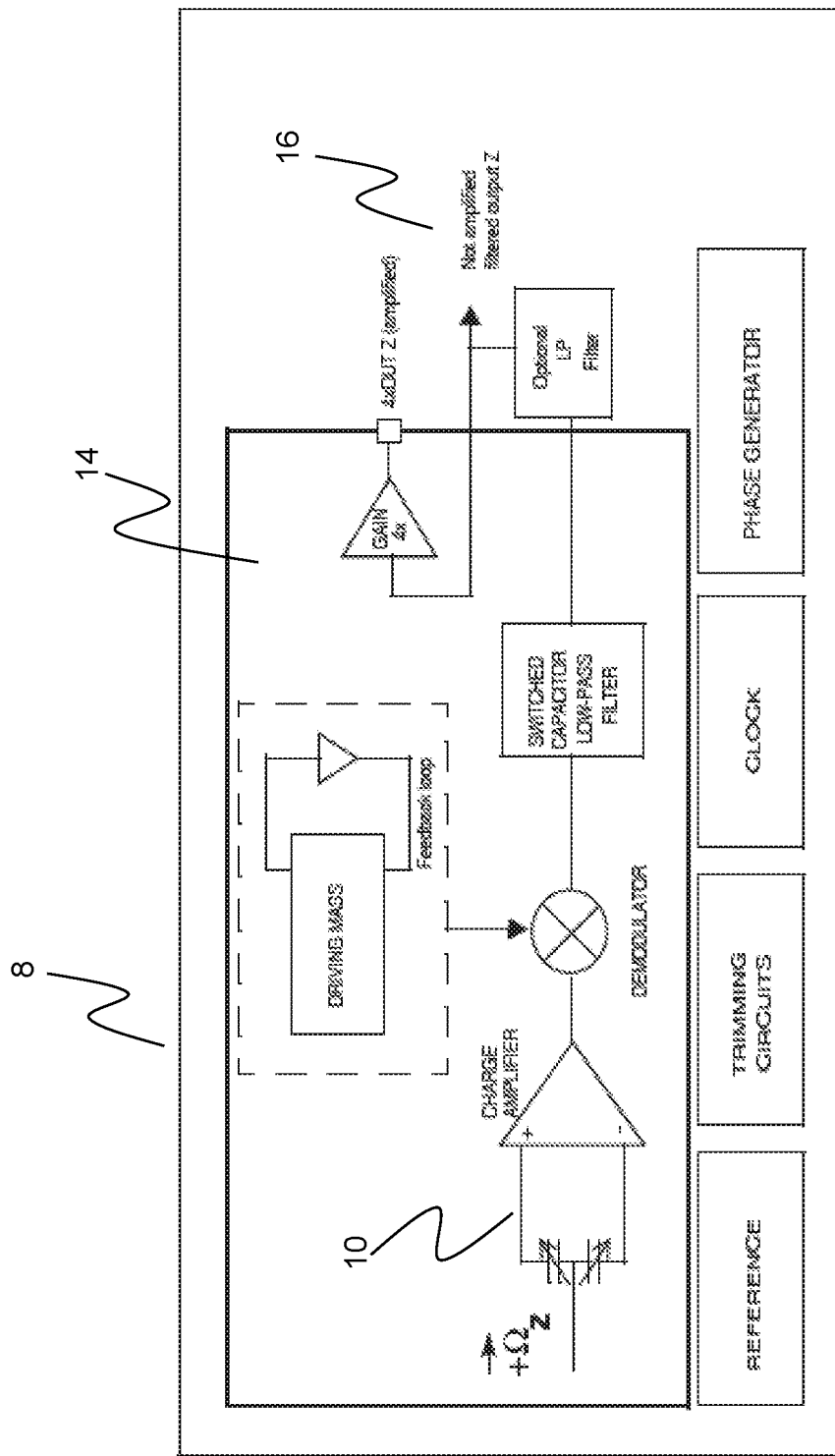
Figure 1C:
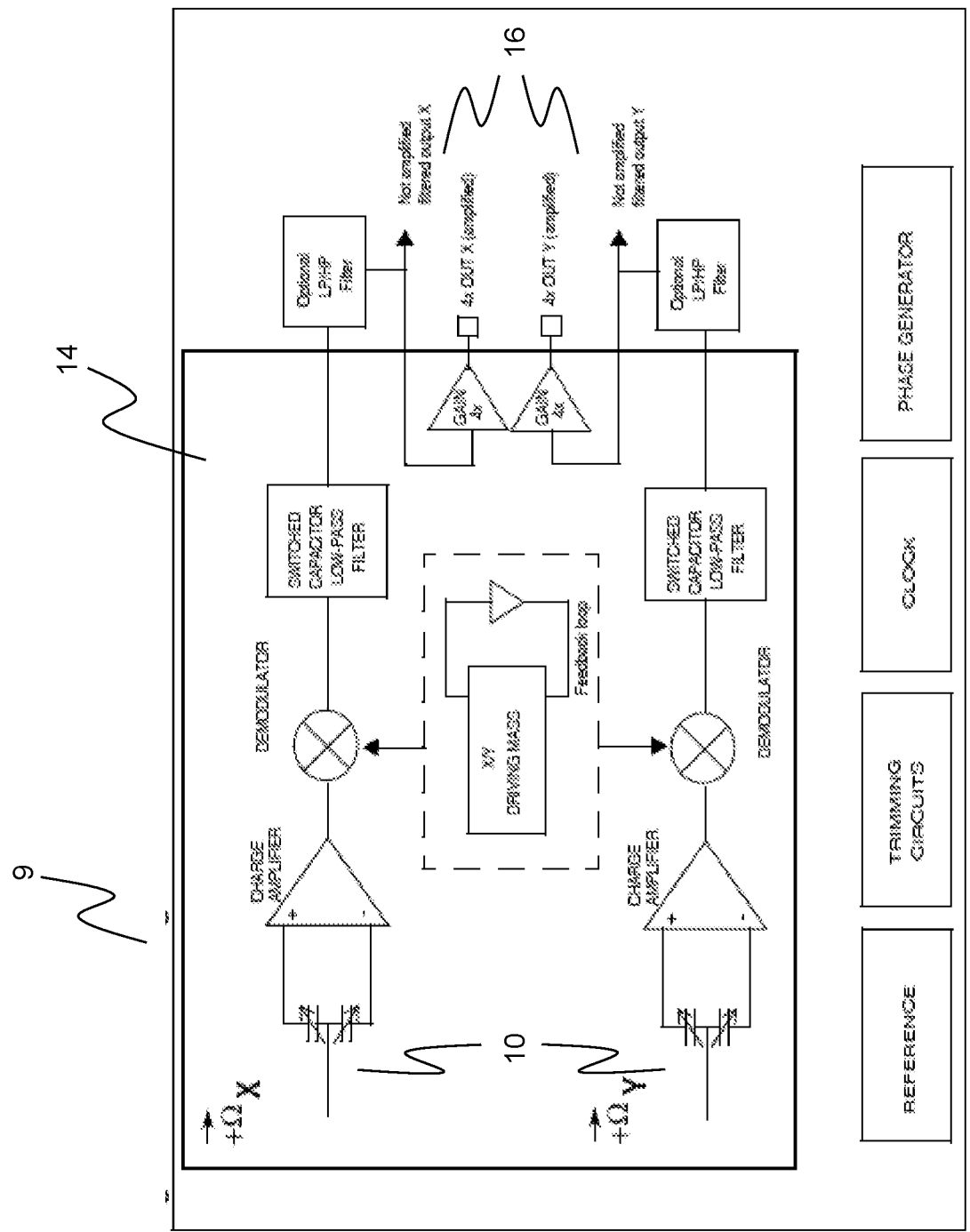

FIGS. 1A and 1B are electrical schematic diagrams for two embodiments of a single-axis gyroscope 8 used as a sensor or in a sensor of the present invention. The sensor element 10 functions on the principle of the Coriolis Effect and a capacitive-based sensing system. Rotation of the sensor 10 causes a shift in response of an oscillating silicon structure resulting in a change in capacitance. An application specific integrated circuit (ASIC) 14, using a standard complimentary metal oxide semiconductor (CMOS) manufacturing process, detects and transforms changes in capacitance into an analog output voltage 16, which is proportional to angular rate. The sensor element design utilizes differential capacitors and symmetry to significantly reduce errors from acceleration and off-axis rotations. FIG. 1C is an electrical schematic for one embodiment of a dual axis gyroscope 9 also based on the Coriolis Effect as described for FIGS. 1A and 1B. The preferred three axis combination can be achieved by any combination and orientation of three single-axis sensors, a single-axis and dual-axis sensor, a single three-axis sensor (not shown for a gyroscope), two dual-axis sensors where the repeated axis is averaged, or other combinations and orientations known to those skilled in the art which produce orthogonal yaw, pitch, and roll measurements.

Figure 2A:
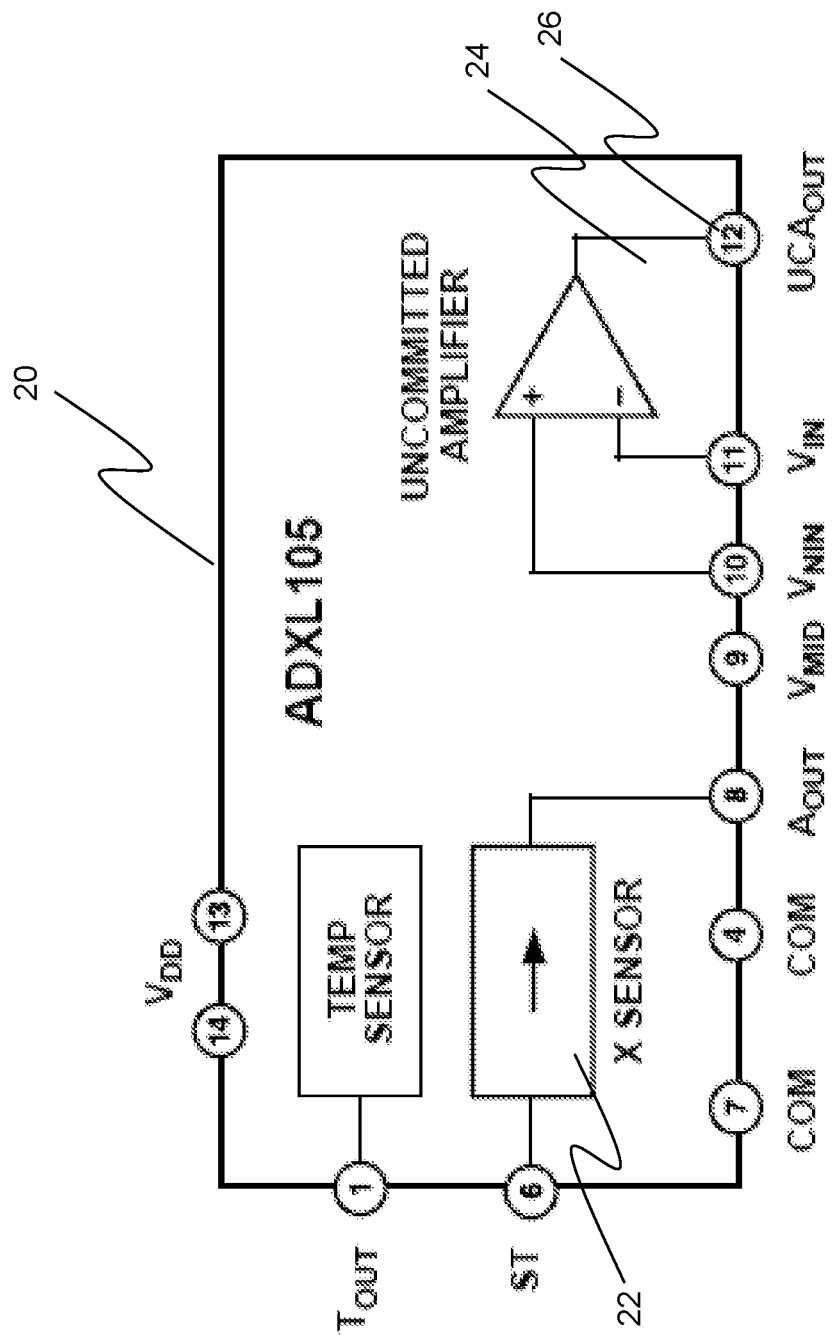
FIGS. 2A-C. Electrical schematics of accelerometers useful in the present invention: A) single-axis accelerometer; B) dual-axis accelerometer; and C) three-axis accelerometer.

FIG. 2A is an electrical schematic diagram for one embodiment of a single axis accelerometer of the present invention. The accelerometer 20 is fabricated using a surface micro-machining process. The fabrication technique uses standard integrated circuit manufacturing methods enabling all signal processing circuitry to be combined on the same chip with the sensor 22. The surface micromachined sensor element 22 is made by depositing polysilicon on a sacrificial oxide layer that is then etched away leaving a suspended sensor element. A differential capacitor sensor is composed of fixed plates and moving plates attached to the beam that moves in response to acceleration. Movement of the beam changes the differential capacitance, which is measured by the on chip circuitry. All the circuitry 24 needed to drive the sensor and convert the capacitance change to voltage is incorporated on the chip requiring no external components except for standard power supply decoupling. Both sensitivity and the zero-g value are ratiometric to the supply voltage, so that ratiometric devices following the accelerometer (such as an analog to digital converter (ADC), etc.) will track the accelerometer if the supply voltage changes. The output voltage (VOUT) 26 is a function of both the acceleration input and the power supply voltage (VS).

Figure 2B:
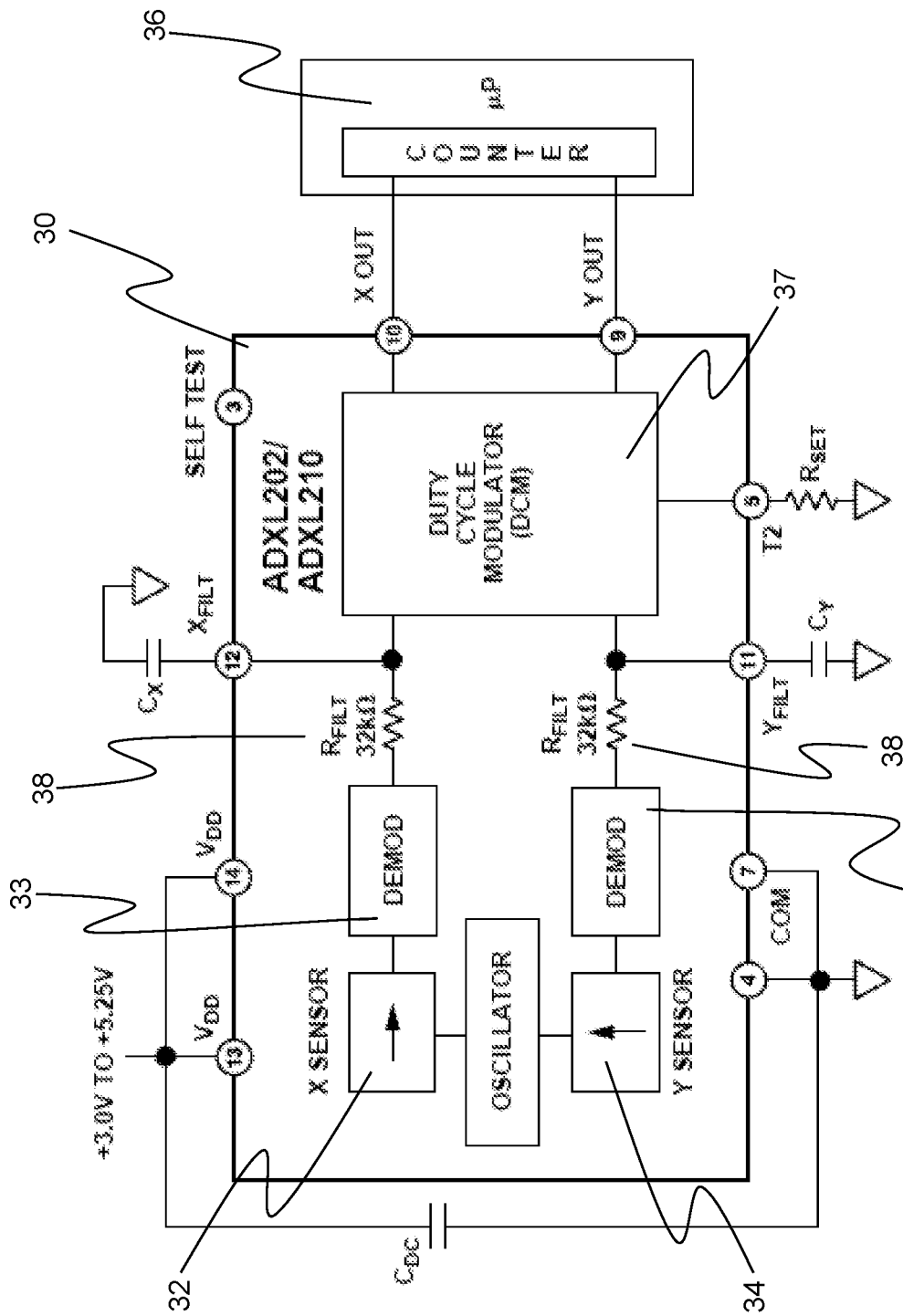

FIG. 2B is an electrical schematic diagram for one embodiment of a dual axis accelerometer of the present invention. The dual axis acceleration measurement system 30 is on a single monolithic IC. They contain a polysilicon surface-micromachined sensor and signal conditioning circuitry to implement an open-loop acceleration measurement architecture. For each axis 32, 34 an output circuit converts the analog signal to a duty cycle modulated (DCM) digital signal that can be decoded with a counter/timer port 36 on a microprocessor. The dual axis accelerometer is capable of measuring both positive and negative accelerations. The sensor 30 is a surface micromachined polysilicon structure built on top of the silicon wafer. Polysilicon springs suspend the structure over the surface of the wafer and provide a resistance against acceleration forces. Deflection of the structure is measured using a differential capacitor that consists of independent fixed plates and central plates attached to the moving mass. The fixed plates are driven by 180-degree out of phase square waves. Acceleration will deflect the beam and unbalance the differential capacitor, resulting in an output square wave whose amplitude is proportional to acceleration. Phase sensitive demodulation techniques are then used to rectify the signal and determine the direction of the acceleration. The output of the demodulator 33, 35 drives a duty cycle modulator (DCM) 37 stage through a 32 kOhm resistor 38. At this point a pin is available on each channel to allow the user to set the signal bandwidth of the device by adding a capacitor. This filtering improves measurement resolution and helps prevent aliasing. After being low-pass filtered, the analog signal is converted to a duty cycle modulated signal by the DCM stage 37. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller.

Figure 2C:
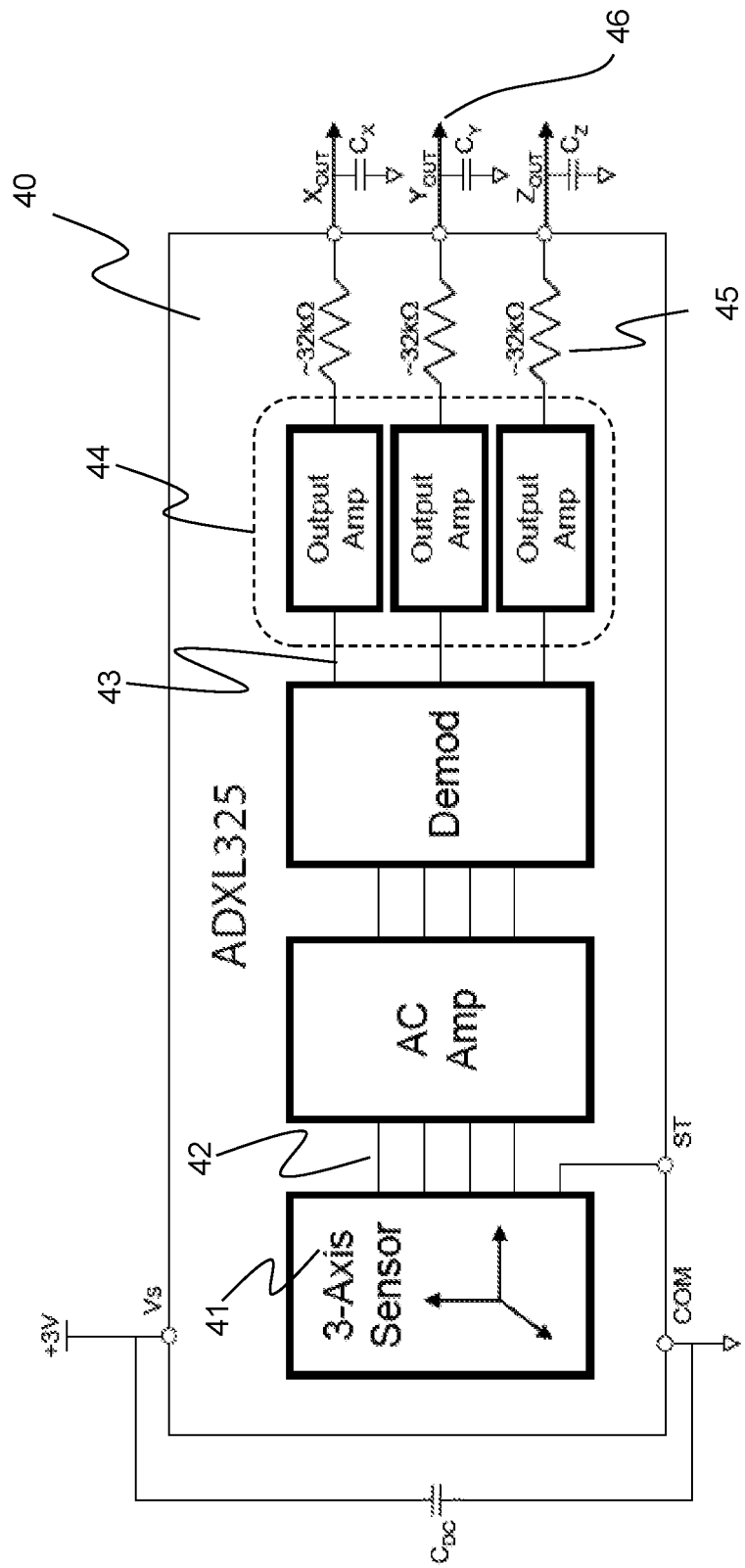

FIG. 2C is an electrical schematic diagram for one embodiment of a three-axis accelerometer of the present invention. The three-axis accelerometer system 40 contains a polysilicon surface micromachined sensor 41 and signal conditioning circuitry to implement an open-loop acceleration measurement architecture. The sensor is a polysilicon surface micromachined structure built on top of a silicon wafer. Polysilicon springs suspend the structure over the surface of the wafer and provide a resistance against acceleration forces. Deflection of the structure is measured using a differential capacitor that consists of independent fixed plates and plates attached to the moving mass. The fixed plates are driven by 180° out-of-phase square waves. Acceleration deflects the moving mass and unbalances the differential capacitor resulting in an analog sensor output 42 whose amplitude voltage is proportional to acceleration. Phase-sensitive demodulation techniques are then used to determine the magnitude and direction of the acceleration. The demodulator output 43 is amplified 44 and brought off-chip through a 32 kΩ resistor 45. The user may then set the signal bandwidth of the device by adding a capacitor 46. This filtering improves measurement resolution and helps prevent aliasing. As described for gyroscopes, any combinations and orientations of single, dual, and three-axis accelerometers may be used known to those skilled in the art in order to obtain accelerometric data in three orthogonal directions.

Figure 3:
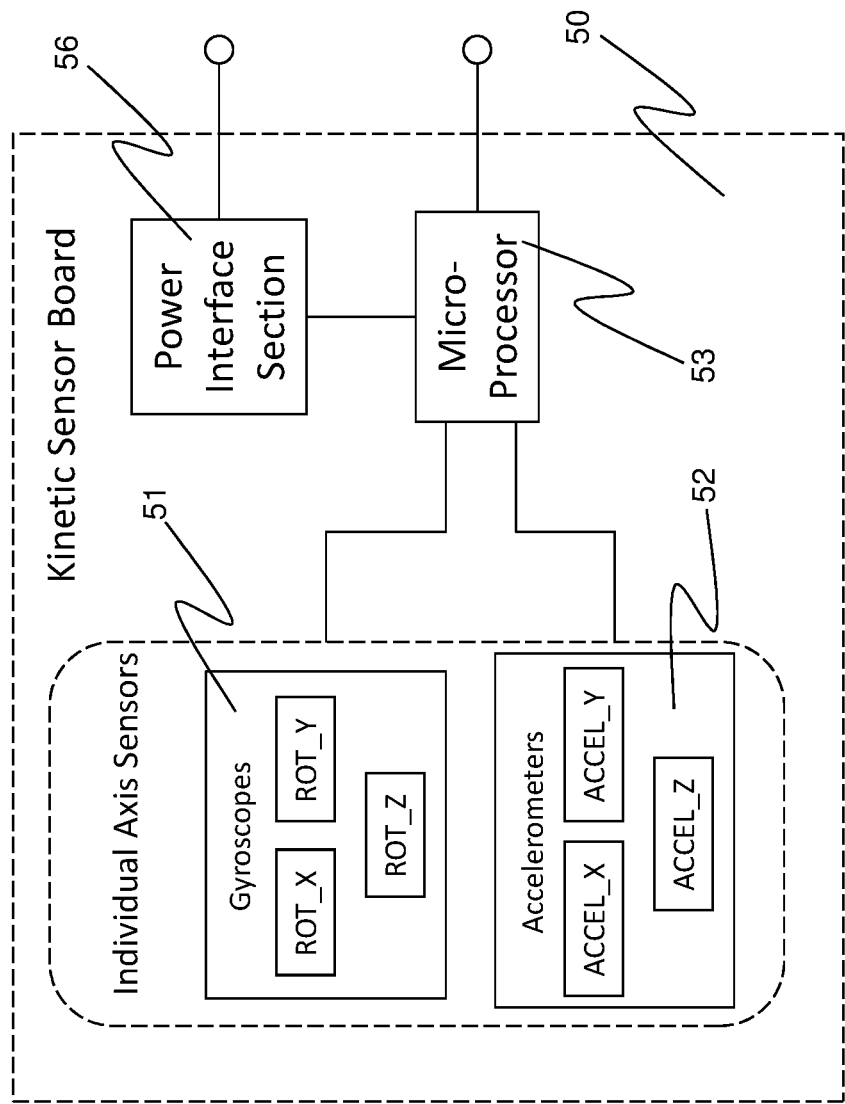
FIG. 3. Block Diagram of the Patient Worn sensor board unit.

FIG. 3 is a block diagram for one embodiment of the subject worn sensor unit. FIG. 3 shows a kinetic sensor board 50 (or subject worn external sensor) of the present invention. The kinetic sensor board 50 is preferably configured with both an accelerometer and a gyroscope for quantifying the subject's motion. In this particular embodiment, the kinetic sensor board 50 consists of three gyroscopes 51 and three orthogonal accelerometers 52. The kinetic sensor board also includes a microprocessor (Texas Instruments mSP430-169) 53 and a power interface section 56.

Figure 4:
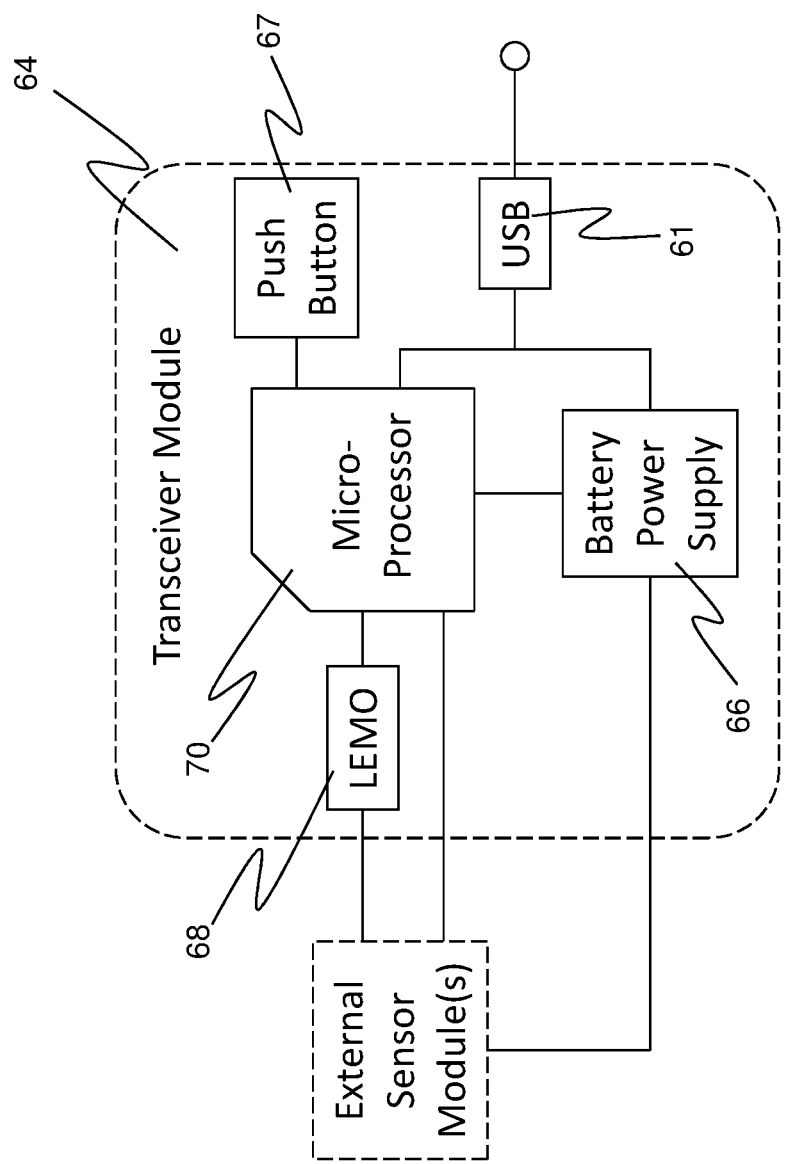
FIG. 4. Block Diagram of the Patient Worn transceiver module unit.

FIG. 4 is a block diagram for one embodiment of the subject worn transceiver module 64. The transceiver module includes a blue tooth radio (not shown, but preferably EB100 A7 Engineering) to provide wireless communications with the patient PC, EMG amplifier and data acquisition circuitry (not shown), on board memory (not shown), a microprocessor 70 (Analog Devices ADUC7020), and a battery power supply (lithium powered) 66 that supplies power to both the transceiver module 64 and one or more external sensor modules 50. The transceiver module also includes a USB port 61 to provide battery recharging and serial communications with the patient PC. The transceiver module also includes a push button input 67. The transceiver module also includes a LEMO connector 68 to attached EMG electrode leads to the module.

Figure 5:
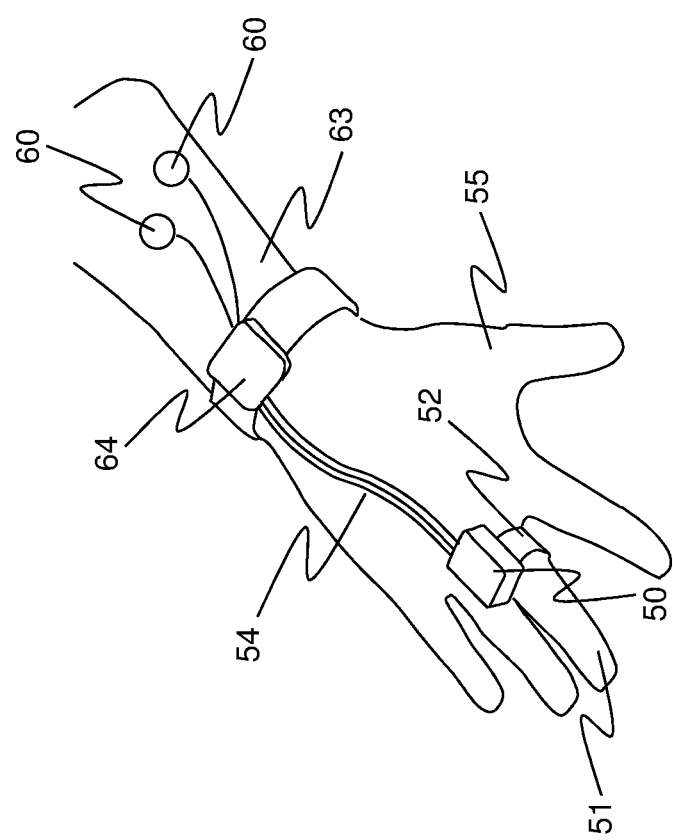
FIG. 5. Schematic showing placement of various components of the movement disorder device with an external sensor module for the hand and EMG electrodes.

FIG. 5 illustrates one possible embodiment of the subject 55 worn components of the system combining the sensor board 50 and the transceiver module 64. The sensor board 50 is worn on the subject's 55 finger 51 and the transceiver module 64 is worn on the subject's 55 wrist 63. The transceiver module 64 and one or more external sensor modules 50 are connected by a thin multi-wire leads 54. The transceiver module 64 in this embodiment connects to one or more electrodes 60 used to measure EMG.

Figure 6:
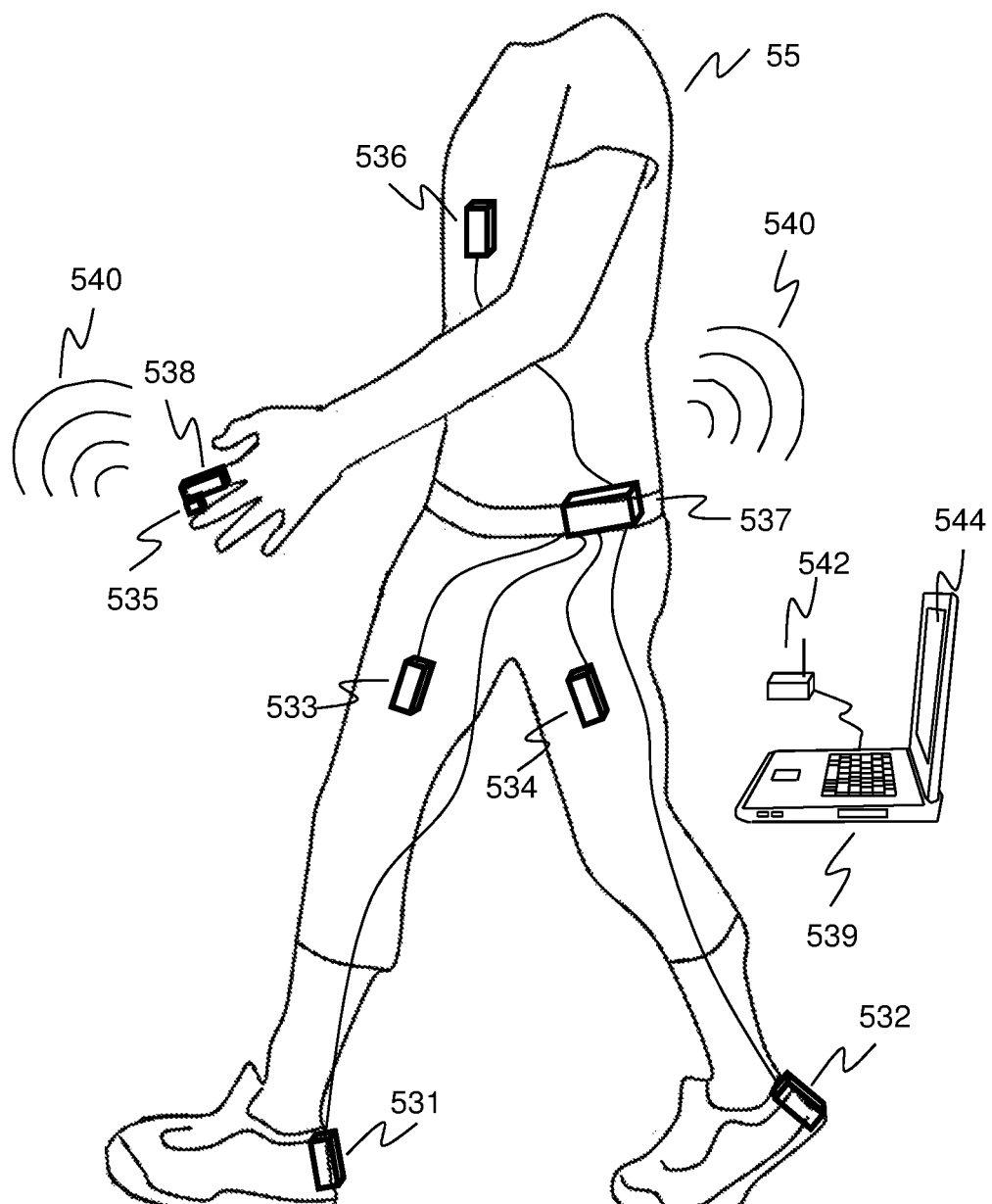
FIG. 6. Graphic depiction of a subject showing possible movement disorder device units over the whole body in different embodiments of the present invention.

FIG. 6 illustrates possible sensor locations of a movement measuring device for different embodiments of the present invention utilizing full body motion. The subject 55 in this particular embodiment is wearing six sensor units 531-536 comprising accelerometers and gyroscopes (both not shown, but described in more detail herein) for recording movement data. The subject 55, in this embodiment, wears at least one sensor unit on a heel 531, 532, thigh 532, 534, finger 535, or torso 536. The subject 55 preferably may wear at least 2 sensor units on a combination of heels 531, 532, thighs 532, 534, fingers 535, or torso 536. The subject 55, in this embodiment, even more preferably may wear at least 4 sensor units on a combination of heels 531, 532, thighs 532, 534, fingers 535, or torso 536. The subject 55, in this embodiment, still even more preferably may wear at least 8 sensor units on a combination of heels 531, 532, thighs 533, 534, fingers 535, joints (not shown), upper appendages (not shown), a waist (not shown), a torso 536, or other useful recording position known to someone skilled in the art. Additionally, a transceiver unit 537-538 for preprocessing and transmitting the movement data may be wired or wireless with respect to both the sensors and an external processor 539. The movement data from the transceiver unit 537 or 538 is either stored for transfer at a later time or for immediate transmission to a receiver unit 542 on the external processing unit via various mediums and any transmission protocols, for example, radio link 540, or by Bluetooth, WIFI, or even USB (not shown), or the like. The processor (not shown) of the external processing unit 539 feeds the data into a trained algorithm preferably loaded into the processor. The trained algorithm preferably correlates with a central database 220 and outputs a patient customized treatment which may then be displayed on a monitor 544 or as input to control a treatment device such as an electric stimulator, automated medicine delivery or titration device, or the like.

Figure 7:
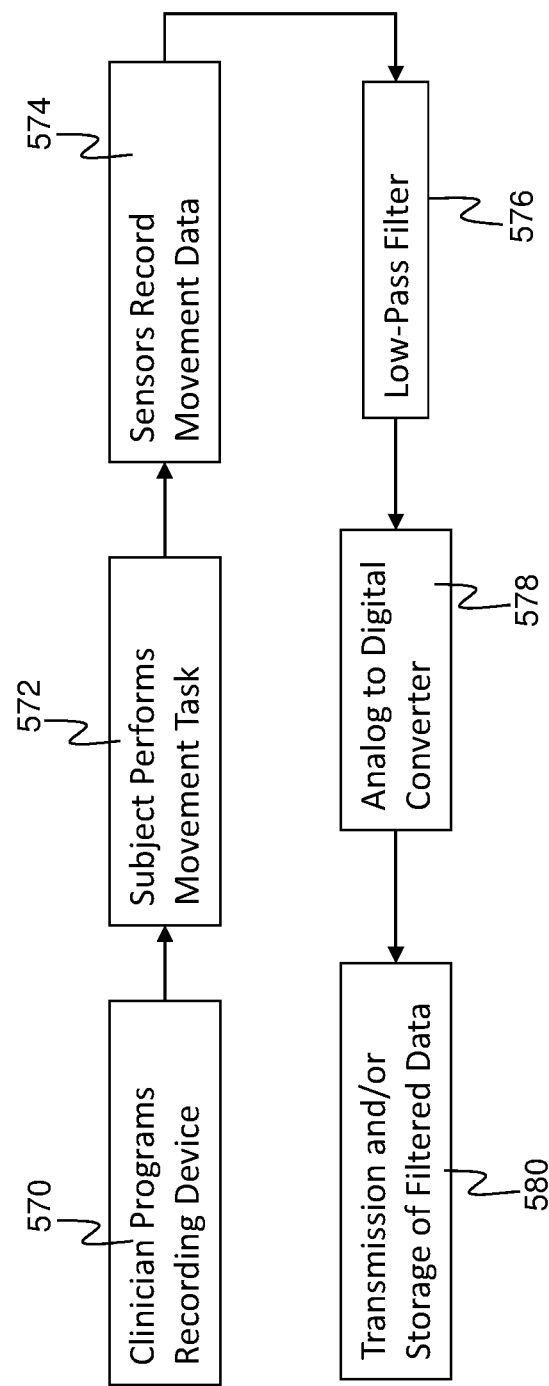
FIG. 7. Flow chart of preferable preprocessing steps.

FIG. 7 depicts preferable steps for preprocessing recorded movement data before extracting kinematic features or correlating it with a central database in order to determine a patient's treatment. Preferably this preprocessing is contained within the movement measuring apparatus, such as part of the transceiver unit, and consists of one or more electronic components. In various embodiments, a clinician first programs the recording device 570 to measure only at specific times or from specific sensors, or even to measure continuously. Next, the subject performs movement tasks 572 according to the clinician's orders, either during specified tasks at the clinician's office, or at home during activities of daily living. While performing these tasks, the sensors of the movement measuring apparatus, preferably a combination of accelerometers and gyroscopes, record the subject's movement data 574. Once the movement data is recorded, preferably a low pass filter 576 is then used to remove all artifacts (including movement and electrical interference) or information known to those skilled in the art which would be unrelated to the subject's movement. Preferably the low pass filter allows only frequencies less than 100 Hz. Even more preferably, the low pass filter allows only frequencies less than 50 Hz. Even more preferably, the low pass filter allows only frequencies less than 30 Hz. Still more preferably, the low pass filter allows only frequencies less than 20 Hz. Next, an analog to digital converter (ADC) 578 may be used to digitize the data for future processing. Preferably, the ADC samples the recorded movement data at a rate of 128 Hz. Finally, the filtered data is either immediately transmitted or stored on board for later transmission 580 to a central database 220 or processor for use by a trained treatment customization algorithm.

Figure 8:
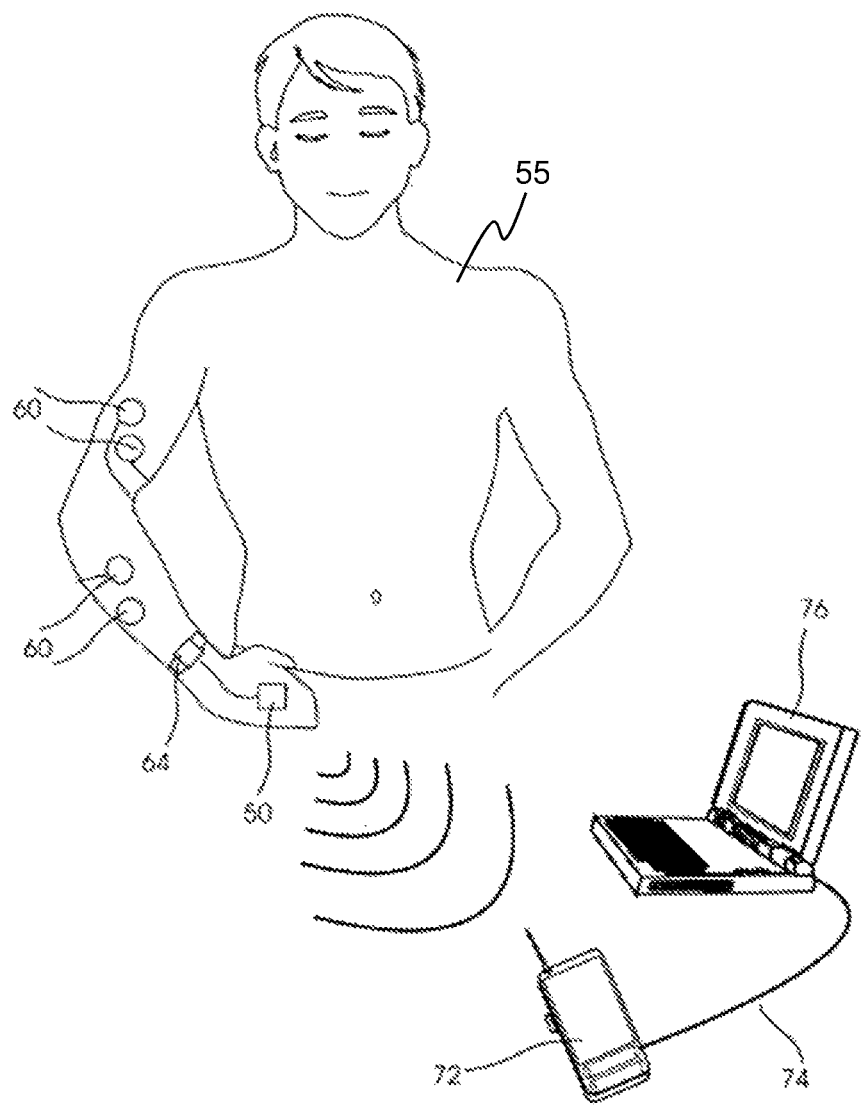
FIG. 8. Schematic showing various system components of the movement disorder device.

FIG. 8 illustrates one embodiment of the system components of the wireless movement disorder monitor. The external sensor module 50 in this embodiment contains three orthogonal accelerometers (not shown) and three orthogonal gyroscopes (not shown). This input to the external sensor module 50 consists of the kinetic forces applied by the user and measured by the accelerometers and gyroscopes. The output from the board is linear acceleration and angular velocity data in the form of output voltages. These output voltages are input to the transceiver module 64. These voltages undergo signal conditioning and filtering before sampling by an analog to digital converter. This digital data is then stored in on board memory and/or transmitted as a packet in RF transmission by a blue tooth transceiver. Additionally, EMG electrodes 60 worn by the subject may be input to the transceiver module. An amplifier on the transceiver module 64 amplifies the EMG signal(s) before signal conditioning, filtering, and sampling by the analog to digital converter. The EMG data is also stored in the on board memory and/or contained in the packet for RF transmission. A microprocessor (not shown) in the transceiver module 64 controls the entire process. Kinetic and EMG data packets may be sent by RF transmission to a nearby computer transceiver 72 which receives the data using an embedded blue tooth radio to a computer 76. Kinetic and EMG data may also be stored on the on board memory and downloaded to a computer 76 at a later time. The computer 76 then processes, analyzes, and stores the data. The kinetic sensor board 50 measures accelerations along and angular velocities about each of three orthogonal axes. The signals from the accelerometers and gyroscopes of the kinetic sensor board 50 are preferably input into a processor for signal conditioning and filtering. Preferably, a combination of three axes of gyroscopes as discussed in FIG. 1 are utilized on the kinetic sensor board with an input range of at least 1500 degrees/second. Specific parts, the LPR5150AL and LY5150ALH (a dual and single axis gyroscope, respectively) from STMicroelectronics, were selected after an analysis of cost, size and power consumption. The land grid array type of component was selected to minimize size. Additionally, a MEMS technology three-axis accelerometer, from Analog Devices (ADXL325), was employed to record accelerations along the orthogonal x, y, and z-axes. The sensors provide full-scale range of ±5 g, low noise (250 ug/sqrt (Hz)), and low power (typically 350 uA per axis) in a surface mount package. Other combinations of accelerometers and gyroscopes known to those skilled in the art could also be used. A lightweight plastic housing was then used to house the sensor for measuring the subject's external body motion. The external body motion sensor(s) can be worn on the subject's finger, hand, wrist, fore arm, upper arm, head, chest, back, waist, legs, thighs, feet, ankles, heels, toes, and/or the like.

Various embodiments of the present invention may include a sensor(s) for measuring the subject's electrical muscle activity through techniques such as electromyography (EMG) or the like. FIG. 8 shows the EMG electrodes 60 which are connected to an amplifier 62. With an EMG sensor, a voltage difference or difference in electrical potential is measured between at least two recording electrodes. The electrodes used can be any type known to those skilled in the art including both indwelling (needle), surface and dry electrodes. Typical EMG electrodes connections may have an impedance in the range of from 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out and no skin to abrade or clean. Additionally if electrodes are used as the sensor(s), preferably at least three electrodes are used-two signal electrodes and one reference electrode.

Preferably, the transceiver module 64 contains one or more electronic components such as the microprocessor 70 for detecting both the signals from the gyroscopes 51 and accelerometers 52, and for detecting the signal from an EMG electrode 60. Preferably, the one or more electronic components also filter (and possibly amplify) the detected EMG signals and kinetic motion signals, and more preferably convert these signals, which are in an analog form into a digital signal for transmission to the remote receiving unit. The one or more electronic components are attached to the subject as part of device or system. Further preferably, the one or more electronic components can receive a signal from the remote receiving unit or other remote transmitters. The one or more electronic components may include circuitry for but are not limited to for example electrode amplifiers, signal filters, analog to digital converter, blue tooth radio, a DC power source and combinations thereof. The one or more electronic components may comprise one processing chip, multiple chips, single function components or combinations thereof, which can perform all of the necessary functions of detecting a kinetic or physiological signal from the electrode, storing that data to memory, uploading data to a computer through a serial link, transmitting a signal corresponding to a kinetic or physiological signal to a receiving unit and optionally receiving a signal from a remote transmitter. These one or more electronic components can be assembled on a printed circuit board or by any other means known to those skilled in the art. Preferably, the one or more electronic components can be assembled on a printed circuit board or by other means so its imprint covers an area less than 4 in$^2$, more preferably less than 2 in$^2$, even more preferably less than 1 in$^2$, still even more preferably less than 0.6 in$^2$, and most preferably less than 0.25 in$^2$.

Preferably, the circuitry of the one or more electronic components is appropriately modified so as to function with any suitable miniature DC power source. More preferably, the DC power source is a battery. The most preferred battery of the present invention is lithium powered batteries. Lithium ion batteries offer high specific energy (the number of given hours for a specific weight), which is preferable. Additionally, these commercially available batteries are readily available and inexpensive. Other types of batteries include but are not limited to primary and secondary batteries. Primary batteries are not rechargeable since the chemical reaction that produces the electricity is not reversible. Primary batteries include lithium primary batteries (e.g., lithium/thionyl chloride, lithium/manganese dioxide, lithium/carbon monofluoride, lithium/copper oxide, lithium/iodine, lithium/silver vanadium oxide and others), alkaline primary batteries, zinc-carbon, zinc chloride, magnesium/manganese dioxide, alkaline-manganese dioxide, mercuric oxide, silver oxide as well as zinc/air and others. Rechargeable (secondary) batteries include nickel-cadmium, nickel-zinc, nickel-metal hydride, rechargeable zinc/alkaline/manganese dioxide, lithium/polymer, lithium-ion and others.

Preferably, the circuitry of the one or more electronic components comprises data acquisition circuitry further including an amplifier that amplifies the EMG, (The gyroscope and accelerometer signals will not need to be amplified). The data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

More preferably, a low-noise, lower power instrumentation amplifier is used. The inputs for this circuitry is guarded with preferably, external ESD/EMI protection, and very high-impedance passive filters to reject DC common-mode and normal-mode voltages. Still preferably, the instrumentation amplifier gain can be adjusted from unity to approximately 100 to suit the requirements of a specific application. If additional gain is required, it preferably is provided in a second-order anti-bias filter, whose cutoff frequency can be adjusted to suit a specific application, with due regard to the sampling rate. Still preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Preferably, the signals are converted to a digital form. This can be achieved with an electronic component or processing chip through the use of an ADC. More preferably, the ADC restricts resolution to 16-bits due to the ambient noise environment in such chips. Despite this constraint, the ADC remains the preferable method of choice for size-constrained applications such as with the present invention unless a custom data acquisition chip is used because the integration reduces the total chip count and significantly reduces the number of interconnects required on the printed circuit board.

Preferably, the circuitry of the sensor board comprises a digital section. More preferably, the heart of the digital section of the sensor board is the Texas Instruments MSP430-169 microcontroller. The Texas Instruments MSP430-169 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry of the transceiver module comprises a digital section. More preferably, the heart of the digital section of the sensor board is the Analog Devices ADUC7020 microcontroller. The Analog Devices ADUC7020 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry for the one or more electronic components is designed to provide for communication with external quality control test equipment prior to sale, and more preferably with automated final test equipment. In order to supply such capability without impacting the final size of the finished unit, one embodiment is to design a communications interface on a separate PCB using the SPI bus with an external UART and level-conversion circuitry to implement a standard serial interface for connection to a personal computer or some other form of test equipment. The physical connection to such a device requires significant PCB area, so preferably the physical connection is designed to keep the PCB at minimal imprint area. More preferably, the physical connection is designed with a break-off tab with fingers that mate with an edge connector. This allows all required final testing and calibration, including the programming of the processing chip memory, can be carried out through this connector, with test signals being applied to the analog inputs through the normal connections which remain accessible in the final unit. By using an edge fingers on the production unit, and an edge connector in the production testing and calibration adapter, the system can be tested and calibrated without leaving any unnecessary electronic components or too large an PCB imprint area on the final unit.

Preferably, the circuitry for the one or more electronic components comprises nonvolatile, rewriteable memory. Alternatively, if the circuitry for the one or more electronic components doesn't comprise nonvolatile, rewriteable memory then an approach should be used to allow for reprogramming of the final parameters such as radio channelization and data acquisition and scaling. Without nonvolatile, rewriteable memory, the program memory can be programmed only once. Therefore one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration. When the final parameters have been determined, the next area is programmed with these parameters. If the final testing and calibration reveals problems, or some other need arises to change the values, additional variations of the parameters may be programmed. The firmware of various embodiments of the present invention scans for the first blank configuration block and then uses the value from the preceding block as the operational parameters. This arrangement allows for reprogramming of the parameters up to several dozen times, with no size penalty for external EEPROM or other nonvolatile RAM. The circuitry for the one or more electronic components has provisions for in-circuit programming and verification of the program memory, and this is supported by the breakoff test connector. The operational parameters can thus be changed up until the time at which the test connector is broken off just before shipping the final unit. Thus the manufacturability and size of the circuitry for the one or more electronic components is optimized.

Preferably the circuitry of the one or more electronic components includes an RF transmitter. Still preferably includes a Bluetooth radio system utilizing the EB100 component from A7 engineering. Another feature of the circuitry of the one or more electronic components preferably is an antenna. The antenna, preferably, is integrated in the rest of the circuitry. The antenna can be configured in a number of ways, for example as a single loop, dipole, dipole with termination impedance, logarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if a RF transmitter and receiver are used on the electrode patch, and polarization-sensitive antennas in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing chip or into one or more of the other electronic components, whereby the antenna is preferably realized by means of thin film technology. The antenna can serve to just transfer data or for both transferring data to and for receiving control data received from a remote communication station which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the electrode patch and/or the remote communication station. The couplers being used to measure the radiated or reflected radio wave transmission output. Any damage to the antenna (or also any faulty adaptation) thus can be registered, because it is expressed by increased reflection values.

An additional feature of the present invention is an optional identification unit. By allocating identification codes-a patient code, the remote communication station is capable of receiving and transmitting data to several subjects, and for evaluating the data if the remote communication station is capable of doing so. This is realized in a way such that the identification unit has control logic, as well as a memory for storing the identification codes. The identification unit is preferably programmed by radio transmission of the control characters and of the respective identification code from the programming unit of the remote communication station to the patient worn unit. More preferably, the unit comprises switches as programming lockouts, particularly for preventing unintentional reprogramming.

In any RF link, errors are an unfortunate and unavoidable problem. Analog systems can often tolerate a certain level of error. Digital systems, however, while being inherently much more resistant to errors, also suffer a much greater impact when errors occur. Thus the present invention when used as a digital system, preferably includes an error control sub architecture. Preferably, the RF link of the present invention is digital. RF links can be one-way or two-way. One-way links are used to just transmit data. Two-way links are used for both sending and receiving data.

If the RF link is one-way error control, then this is preferably accomplished at two distinct levels, above and beyond the effort to establish a reliable radio link to minimize errors from the beginning. At the first level, there is the redundancy in the transmitted data. This redundancy is performed by adding extra data that can be used at the remote communication station or at some station to detect and correct any errors that occurred during transit across the airwaves. This mechanism known as Forward Error Correction (FEC) because the errors are corrected actively as the signal continues forward through the chain, rather than by going back to the transmitter and asking for retransmission. FEC systems include but are not limited to Hamming Code, Reed-Solomon and Golay codes. Preferably, a Hamming Code scheme is used. While the Hamming Code scheme is sometimes maligned as being outdated and underpowered, the implementation in certain embodiments of the present invention provides considerable robustness and extremely low computation and power burden for the error correction mechanism. FEC alone is sufficient to ensure that the vast majority of the data is transferred correctly across the radio link. Certain parts of the packet must be received correctly for the receiver to even begin accepting the packet, and the error correction mechanism in the remote communication station reports various signal quality parameters including the number of bit errors which are being corrected, so suspicious data packets can be readily identified and removed from the data stream.

Preferably, at a second, optional level, an additional line of defense is provided by residual error detection through the use of a cyclic redundancy check (CRC). The algorithm for this error detection is similar to that used for many years in disk drives, tape drives, and even deep-space communications, and is implemented by highly optimized firmware within the electrode patch processing circuitry. During transmission, the CRC is first applied to a data packet, and then the FEC data is added covering the data packet and CRC as well. During reception, the FEC data is first used to apply corrections to the data and/or CRC as needed, and the CRC is checked against the message. If no errors occurred, or the FEC mechanism was able to properly correct such errors as did occur, the CRC will check correctly against the message and the data will be accepted. If the data contains residual errors (which can only occur if the FEC mechanism was overwhelmed by the number of errors), the CRC will not match the packet and the data will be rejected. Because the radio link in this implementation is strictly one-way, rejected data is simply lost and there is no possibility of retransmission.

More preferably, the RF link utilizes a two-way (bi-directional) data transmission. By using a two-way data transmission the data safety is significantly increased. By transmitting redundant information in the data emitted by the electrodes, the remote communication station is capable of recognizing errors and request a renewed transmission of the data. In the presence of excessive transmission problems such as, for example transmission over excessively great distances, or due to obstacles absorbing the signals, the remote communication station is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the remote communication station to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data.

The remote communication station of various embodiments of the present invention can be any device known to receive RF transmissions used by those skilled in the art to receive transmissions of data. The remote communication station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device and/or back. Further optionally, two different remote communication stations can be used, one for receiving transmitted data and another for sending data. For example, with the wireless movement disorder monitoring system of the present invention, the remote communication system of the present invention can be a wireless router, which establishes a broadband Internet connection and transmits the physiological signal to a remote Internet site for analysis, preferably by the subject's physician. Another example is where the remote communication system is a PDA, computer or cell phone, which receives the physiological data transmission, optionally re-processes the information, and re-transmits the information via cell towers, land phone lines or cable to a remote site for analysis. Another example is where the remote communication system is a computer or processor, which receives the data transmission and displays the data or records it on some recording medium, which can be displayed or transferred for analysis at a later time.

The digitized kinetic or physiological signal is then transmitted wirelessly to a remote communication station. This remote communication station allows the subject wide movement. Preferably, the remote communication station can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, still more preferably greater than 500 feet from the subject, even still more preferably greater than about 3000 feet from a subject, even further more preferably greater than about 5000 feet from a subject, and most preferably greater than about 12000 feet from the subject. The remote communication station is used to re-transmit the signal based in part from the physiological signal from the remote communication station wirelessly or via the internet to another monitor, computer or processor system. This allows the physician or monitoring service to review the subjects physiological signals and if necessary to make a determination, which could include modifying the patients treatment protocols.

Optionally, the system of the present invention includes some form of instruction, which can be in written form on paper or on a computer monitor, or on a video. Optionally, a video is used which instructs the subjects to perform a series of tasks during which their kinetic motion and/or EMG can be measured. Since the system of the present invention is preferably used in the subject's home, a video giving directions and/or describing various tasks to be performed by the subject is included with the system. The video may be accessed or viewed for example but not by way of limitation through use of video tape, DVD, as part of computer software provided, through the internet, or the like. The directions could include but are not limited to instructions on how to don the device, how to turn the device on, and the like. The description of various tasks could include but is not limited to exercises which are typically used by a technician, clinician or physician to evaluate a subject with a movement disorder including but not limited to hand grasps, finger tapping exercises, other movements and the like. One embodiment of a video includes the technician, clinician or physician looking into the camera, as they would a patient, and instructing them on device setup, instructing the patients through each of the tasks to be performed, providing verbal encouragement via video after a task, and asking subject's to repeat a task if it was not completed. Preferably, these video clips are edited and converted to a MPEG files using a Pinnacle Studios digital video system that includes a fire-wire card and editing software. For movement disorders such as Parkinson's disease preferably the technician, clinician or physician instructs the user through multiple tasks as per the UPDRS, TRS, or similar scale guidelines including but not limited to rest tremor, postural tremor, action tremor, all bradykinesia tasks (including but not limited to finger taps, hand grasps, and pronation/supination tasks), and/or rigidity tasks. More preferably, if the video is linked to the user interface software, the software will automatically detect if a subject has performed the requested task and provide feedback through the video to either repeat the task or continue to the next task. Still more preferably, once the user has setup the device, it will continually record the subject's movement data (including before and after any directed video tasks), be able to quantify the severity of the subject's symptoms during activities of daily living, and communicate that information with the clinician and subject through interface software, video, or the like.

The present invention includes various methods of measuring and scoring the severity of a subject's movement disorder. These methods include a number of steps which may include but are not limited to measuring a subject's external body motion; transmitting wirelessly a signal based in part on the subject's measured external body motion; receiving the wirelessly transmitted signal; downloading data from memory; and scoring the severity of a subject's movement disorder based in part on the wirelessly transmitted or downloaded signal. Optionally, an electromyogram of the subject's muscle activity may be obtained and used in part to score the severity of the subject's movement disorder.

Figure 9A:
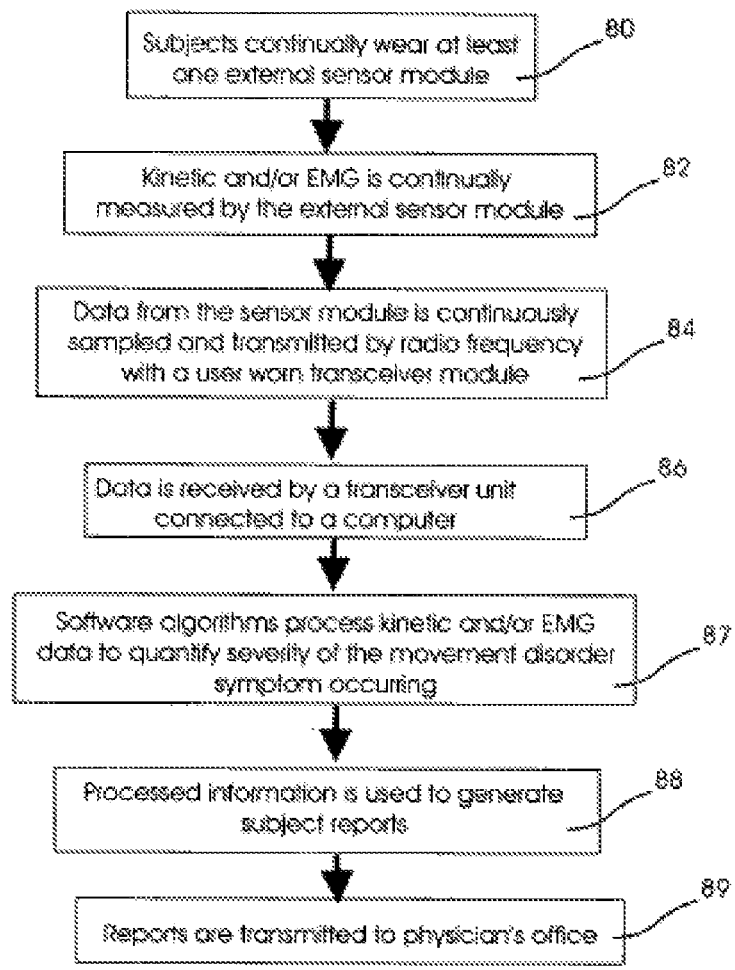
FIGS. 9A-B. Flow diagrams of system in continuous operating mode: A) to generate subject reports; and B) with home monitoring and a central database.
Figure 9B:
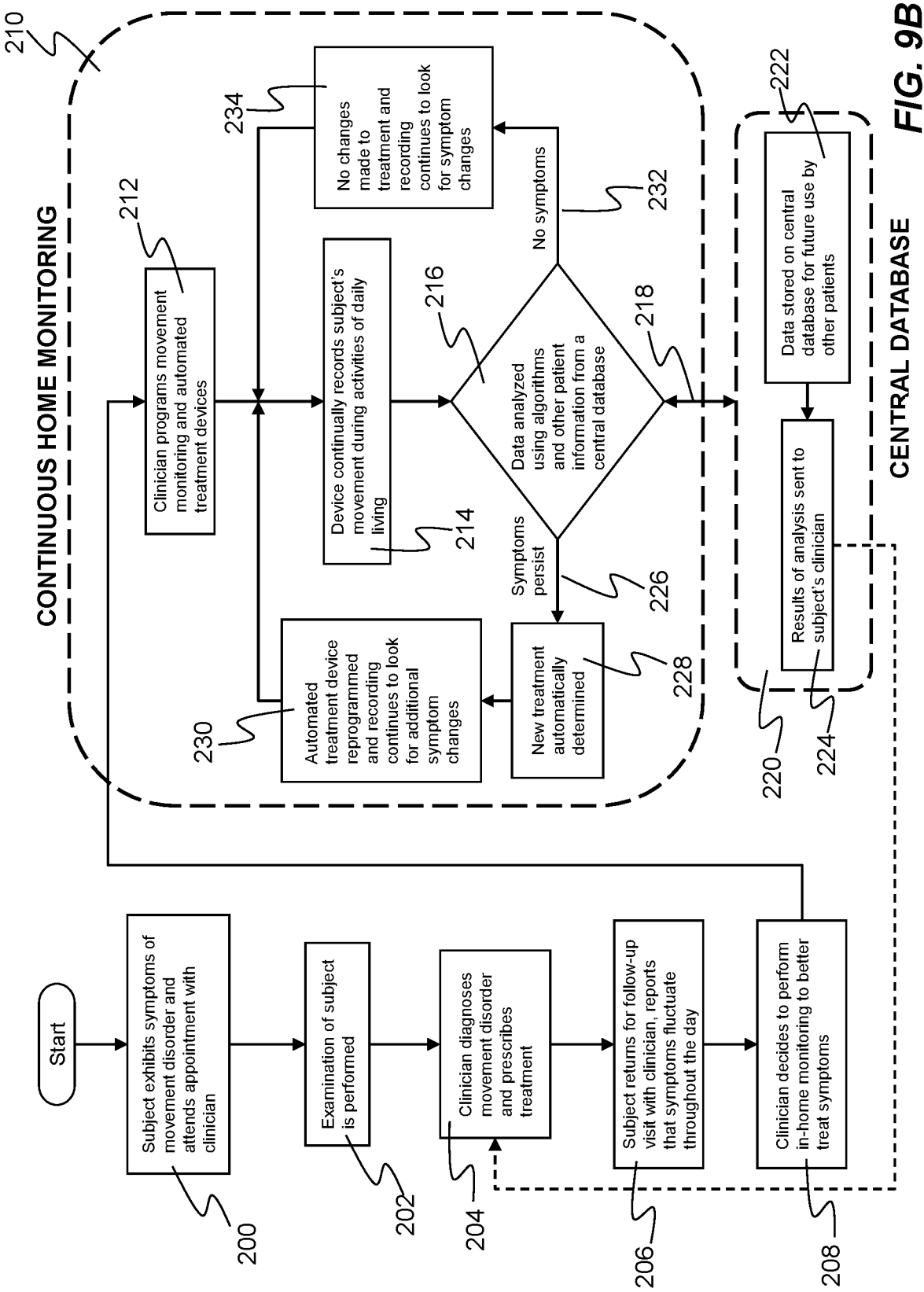

FIGS. 9A-B, 10, and 11 show flow diagrams for various operating modes of the system of the present invention. These operating modes should be viewed as examples but not limitations to the present invention and understood that these are but a few of the methods of using the system of the present invention. FIGS. 9A and 9B are flow diagrams for a continuous operating mode or method for the system of the present invention. In the embodiment of FIG. 9A, the subjects continually wear at least one external sensor module 80. The external sensor module, which can measure kinetic motion and/or EMG is continually measured by the external sensor module 82. Data from the external sensor module is continuously sampled and stored to memory within a subject worn transceiver module 84. During battery recharging of the device when the patient is not wearing the patient components, the patient components are connected through a hardwire USB link to the patient PC. The stored data is then either transmitted via an RF link to a transceiver unit connected to a computer 86 or transferred through the USB port to the computer. Software algorithms in the computer process kinetic and/or EMG data to quantify the severity of the movement disorder symptom occurring 87. The processed information is then used to generate subject reports or data 88, and the reports or data are transmitted to technician, clinician or physician for review 89.

In the continuous operating embodiment of FIG. 9B, a subject initially exhibits symptoms of a movement disorder and attends an appointment with a clinician 200. At the appointment, the clinician examines the subject 202, and upon analysis, diagnosis the subject as having a movement disorder and subsequently orders a treatment 204. At a follow-up visit, the subject may report that symptoms fluctuate greatly throughout the day 206, even while on the prescribed treatment plan. The clinician then decides to perform in-home continual testing 208 to better determine the severity of the subject's symptoms. Continuous home monitoring 210 begins with the clinician programming 212 any movement monitoring devices or automated treatment delivery devices for the subject, or instructing the subject how to do so. The device, containing at least one sensor, preferably an accelerometer or gyroscope of at least three axes, but optionally another sensor capable of measuring motion, such as an EMG, continually records the subject's movement during activities of daily living 214. In addition, the device can include two or more types of sensors, preferably accelerometers and gyroscopes. Activities of daily living may include folding laundry, handwriting, eating, dressing, self-care, and the like. Optionally, the clinician may order the subject to perform clinical tasks such as finger tapping, nose touching, or the like, as defined by standardized scales such as the UPDRS, TRS, and the like, at regularly scheduled periods. Such movement data would also be continually recorded.

A trained algorithm, preferably incorporated by at least one computer processor, analyzes the recorded movement data in real-time 216. The algorithm and processor 216 function to distinguish voluntary motion of activities of daily living or clinician ordered tasks from movement disorder symptoms and quantify their severity. Preferably the trained algorithm and computer processor 216 are also in two-way communication 218 with a central database 220 or multiple databases made up of previous patient movement data, disorder histories, treatment histories, and the like. Preferably two or more databases are used for reading. Such a database 220 would preferably retain information from the current subject for use with future subjects 222 and work with the trained algorithm and processor 216 to determine a recommended treatment for the current subject based on the previous patient data. This database 220 could optionally be used as a real-time gateway for providing updates to the subject's clinician 224 regarding the subject's status.

If the trained algorithm and processor 216 determine that the patient still suffers from movement disorder symptoms 226, a new treatment is determined 228 in conjunction with the central database 220 as previously described. If the subject has an automated treatment delivery device, it is preferably reprogramed according to the new treatment protocol 230. The movement measuring device then continues to record new movement data and the process repeats. If the trained algorithm and processor 216 determine movement disorder symptoms no longer persist 232 then no new treatment is needed, no changes are made 234, and the device continues recording movement data.

Figure 10:
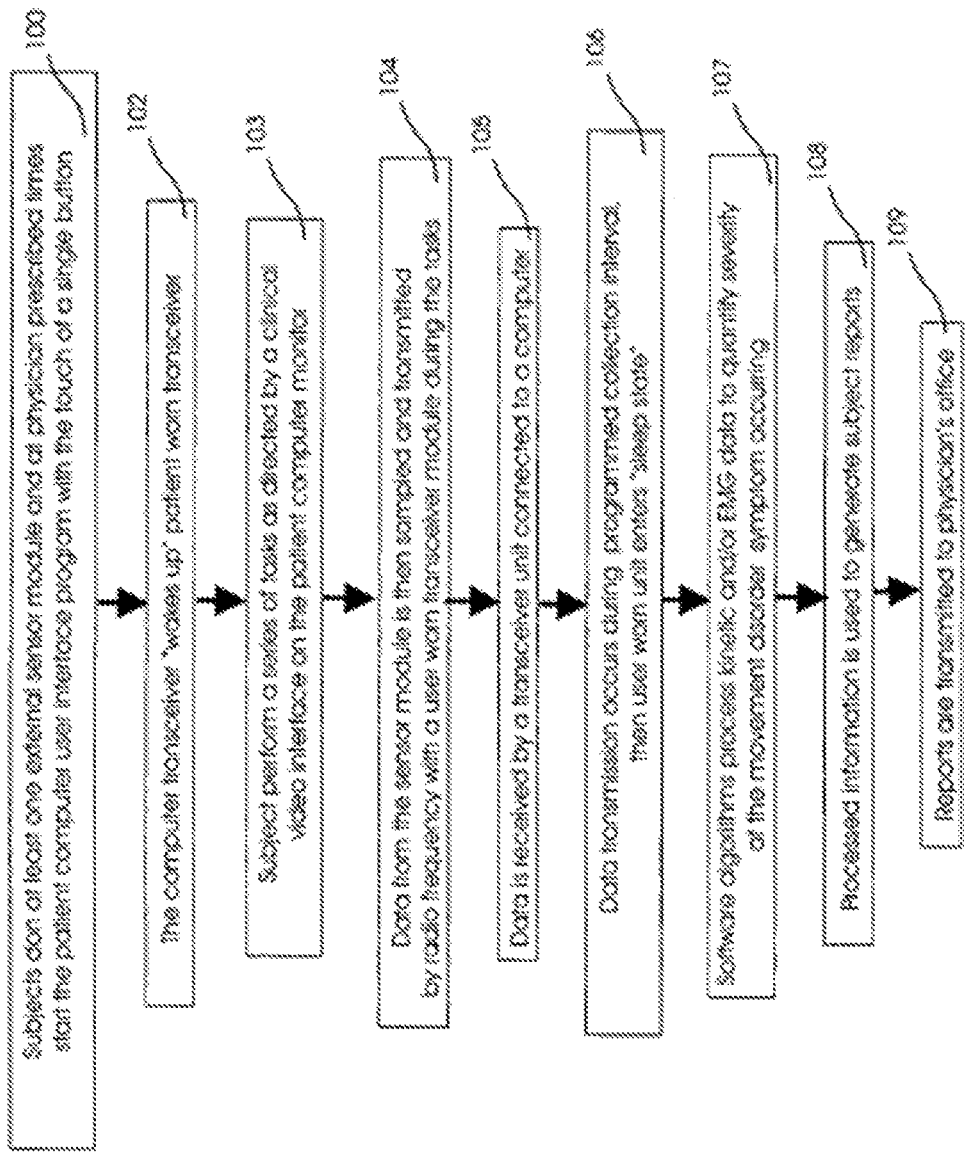
FIG. 10. Flow diagram of system in task operating mode.

FIG. 10 is a flow diagram for a task operating mode or method for the system of the present invention. In this mode the subjects intermittently wear at least one external sensor module at technician, clinician or physician prescribed times 100. The subjects may start the patient computer user interface program, preferably with the touch of a single button. The computer transceiver "wakes up" the subject worn transceiver module 102 or the clinical video on the patient computer instructs the subject to press a button on the transceiver module to manually "wake up" the unit. The subject performs a series of tasks as directed by a clinical video, which preferably is viewed on the patient's computer monitor 103. The data from the external sensor module is then sampled and transmitted by radio frequency with the subject worn transceiver module during the tasks 104. The data is received by a transceiver unit connected to the computer 105. The data transmission lasts approximately or only as long as the same time as a programmed collection interval, the subject worn transceiver unit then enters into a "sleep state" 106. Software algorithms in a computer connected to the computer transceiver unit process the kinetic motion and/or EMG data to quantify severity of the movement disorder symptom occurring 107. The processed information is then used to generate subject reports or data 108, and the reports or data are transmitted to technician, clinician or physician for review 109.

Figure 11:
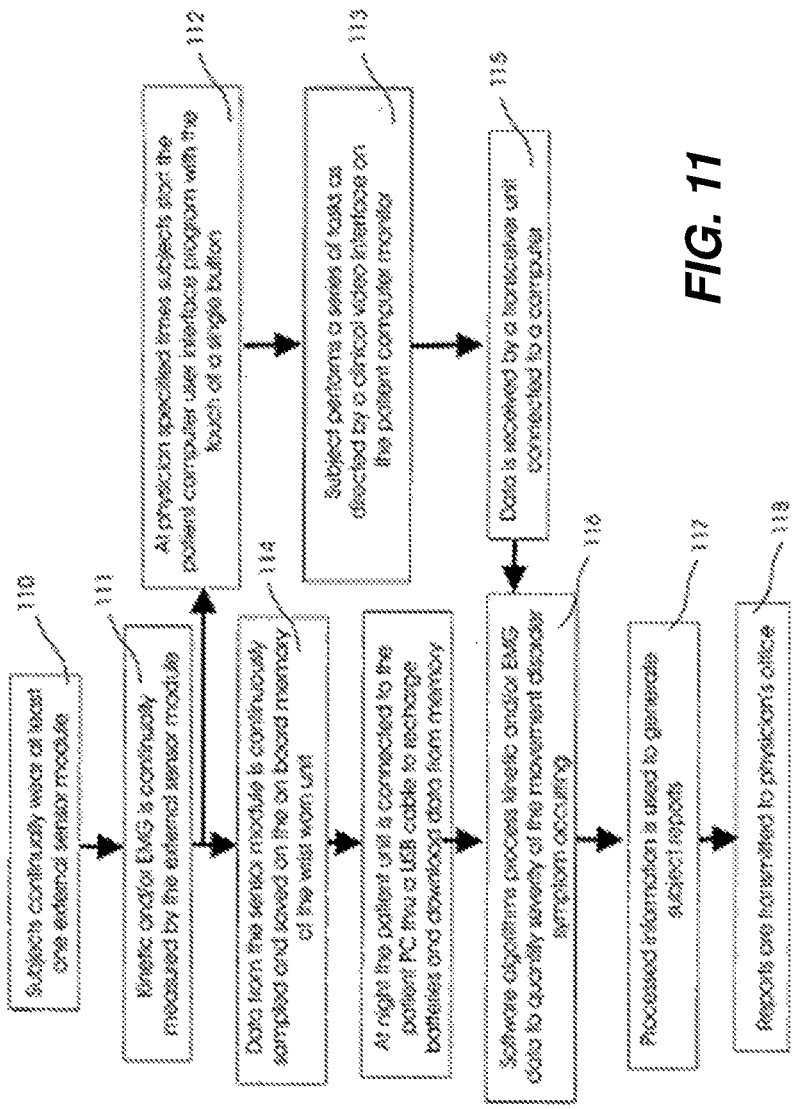
FIG. 11. Flow diagram of system in a combination operating mode.

FIG. 11 is a flow diagram for a combination operating mode or method for the system of the present invention. In this mode, the subject continually wears at least one external sensor module 110. The external sensor module, which can measure kinetic motion and/or EMG is continually measured by the external sensor module 111. Data from the external sensor module is continuously sampled and stored to memory on the subject worn transceiver module 114. This data is then downloaded to the patient computer at a later time. Software algorithms in the computer process kinetic and/or EMG data to quantify the severity of the movement disorder symptom occurring 116. The processed information is then used to generate subject reports or data 117, and the reports or data are transmitted to a technician, clinician or physician for review 118. This method, however, varies from the method described in FIG. 9A in that a technician, clinician, physician or computer at randomly specified times alerts the subject to start or has computer start a video 112, and alerts the subject to perform a series of tasks as directed by the clinical video, which is preferably on the patient's computer monitor 113. During these tasks, data is transmitted by the user worn receiver module and is received by a transceiver unit connected to a computer 115. Software algorithms in the computer process kinetic and/or EMG data to quantify the severity of the movement disorder symptom occurring 116. The processed information is then used to generate subject reports or data 117, and the reports or data are transmitted to the technician, clinician or physician for review 118.

The portable movement disorder device of the present invention for measuring the severity of a subject's movement disorder can be worn in any way likely to provide good data on a subject's movement disorder. Examples would include but are not limited to the use of the device on the subject's finger, hand, wrist, arm; legs, thighs, feet, ankles, heels, toes, torso, and/or head. Preferably, the movement disorder device is on the arm and/or hand of the subject. FIGS. 5 and 8 show a schematic of a movement disorder device on a subject's lower arm and hand. In this embodiment, the subject's kinetic motion is measured by a kinetic sensor board (also known as external sensor module) 50. The external sensor module 50 is held firmly to the subject's finger 51 by a Velcro strap 52. The external sensor module 50 is connected to a subject worn transceiver module 64 via electrical pathways or wires 54. Optionally, the device may also have at least one EMG electrodes (not shown).

Preferably, the subject worn transceiver module in this embodiment is reasonably small size. Achieving the wrist mount design of this embodiment require the size of the radio used for the device be greatly reduced. Preferably, a commercially available chip (Bluetooth technology) is used that can transmit up to 200 ft. Not only will this greatly reduce the size of the device, but the transceiver capability will allow two-way communications between the patient worn unit and the computer unit.

The two-way capability in this particular embodiment will provide multiple benefits. First, by having two-way communications, the unit will be capable of utilizing a protocol where data packets can be re-sent if corrupted during transmission. Another benefit is that several patient worn units could potentially communicate with a single base station clinician PC. In this scenario, the subject units occupy dedicated time slots to transmit their information. Several subject worn units could operate with a single computer base station in a hospital or home setting. Additionally, multiple units may be worn on a subject to monitor tremor in multiple limbs or locations of the body at the same time. FIG. 6 illustrates an embodiment of this concept where the subject wears multiple units on the heels 531-532, thighs 533-534, finger 535, and torso 536. Preferably the sensor units are held firmly to the subject using Velcro straps and are connected to any external modules 537-538, which may also be held firmly to the subject using Velcro straps, via wires. A final benefit of the two-way protocol is that configuration information can be sent to the patient unit over the radio link including power level, frequency, and shut down modes. Shut down modes could be of great benefit for this type of system where the clinical PC can command the subject units to power down between tests thus conserving battery life in the patient unit. Essentially, the technician, clinician, or physician will be able to program the system for continuous recording or to record at certain times for specified intervals.

Preferably, the radio design of this specific embodiment is implemented using a highly integrated radio chip (Bluetooth technology) which requires very few external components, consumes less power than a discrete radio design, and requires less physical area than a discrete design. More preferably, the radio chip takes incoming clock and data and produces a Frequency Modulated carrier when configured as a transmitter, and performs the opposite function when configured as a receiver. This high level of integration makes the only component required to interface to the radio section a unit microcontroller.

With few components and high level of integration, the radio section should be easy to manufacture, have low component cost, and have high field reliability. Preferably, the IC or microprocessor has a controllable RF power output levels and by using the two-way protocol described above, the radio link can operate at a level high enough to ensure reliable data transfer while conserving unit power. Finally, and most preferably, the IC or microprocessor can operate anywhere from 300 MHz to 2.4 GHz providing great flexibility when the system is developed to ensure optimum operation. The 2.4 GHz band is the preferable operating band.

Figure 12:
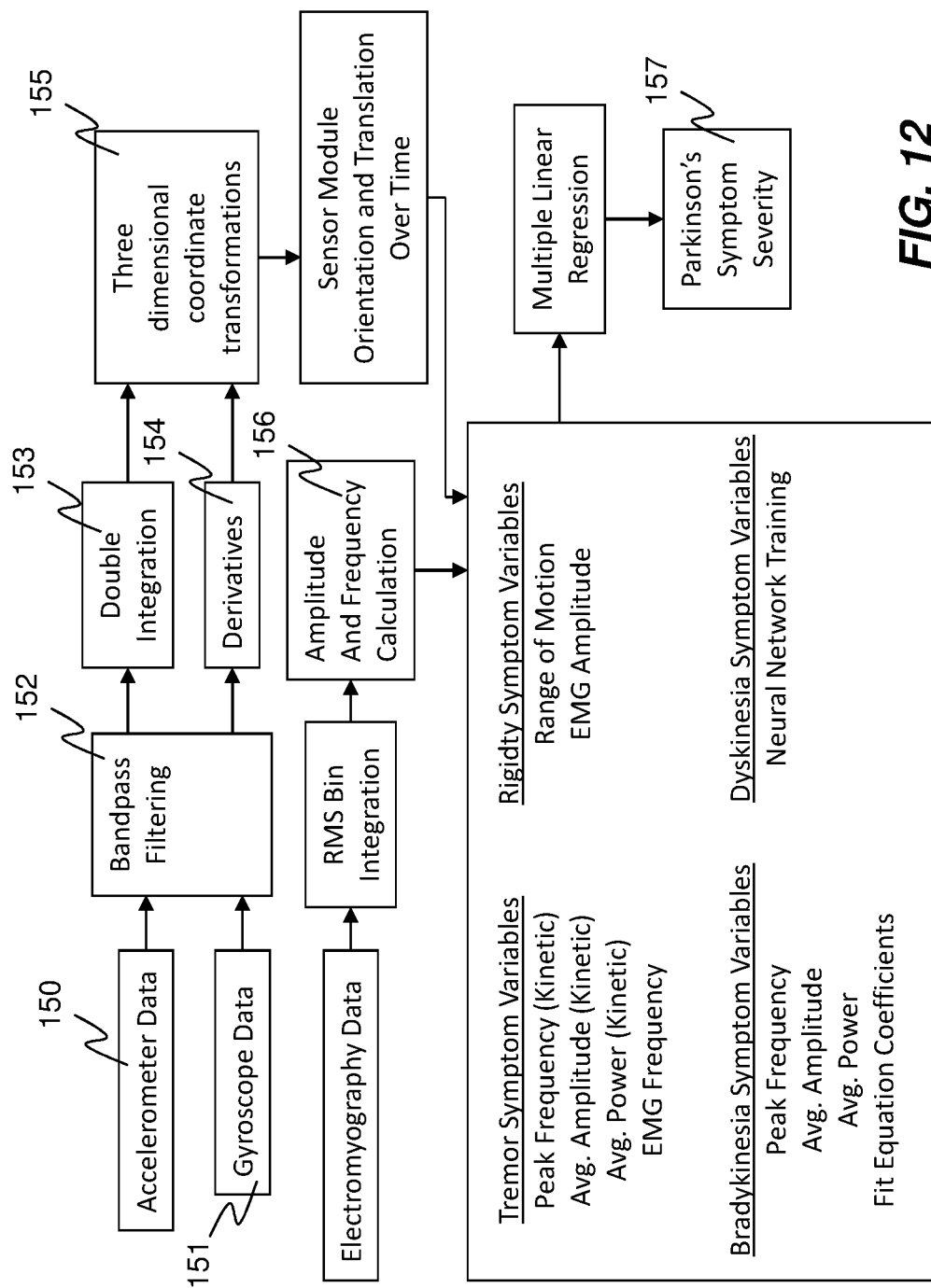
FIG. 12. Flow diagram for one embodiment of the software used in the present invention.

FIG. 12 is a flow diagram for one embodiment of the software used in the present invention. Analog outputs 151, 152 from the accelerometer and gyroscope are converted to linear acceleration and angular velocity with a scaling factor. The linear accelerations and angular velocity inputs are then bandpass filtered 153 to prevent biasing and remove DC drift. The linear acceleration is double integrated to yield linear position. The derivative 154 of the angular velocity is calculated to determine angle. The three dimensional translation and rotation 155 of the module is computed from the information from the three orthogonal accelerometers and three orthogonal gyroscopes. The root mean square (RMS) value of the continuous time EMG signal is calculated over discrete time windows. The amplitude and frequency 156 of the processed EMG signal is calculated. Specific variables are then computed for each Parkinson's symptom based on the processed kinetic and EMG data. Tremor symptom variables may include but are not limited to the peak frequency of the kinetic sensors, the average amplitude of the kinetic sensors, the average power of the kinetic sensors, and the frequency of the EMG signals. Bradykinesia symptom variables may include but are not limited to the peak frequency of EMG or kinetic data, the average amplitude of the kinetic sensors, the average power of the EMG or kinetic sensors, the number of hesitations that occur in a subjects movement, or the linear or exponential fit coefficients used to fit a model to the amplitude of a subject's movement over time. Rigidity symptom variables may include but are not limited to range of motion and EMG amplitude. Dyskinesia symptom variables may include but are not limited to the output of a neural network trained to recognize dyskinesia from other movements using the kinetic sensor data as inputs. The value of each symptom variable for a particular symptom is used in an algorithm that may include but are not limited to multiple linear regression models or neural networks to fit the symptom variables to the qualitative clinicians Unified Parkinson's Disease Rating Scale scores for that symptom 157.

The present invention further includes a treatment delivery system. The treatment delivery system utilizes in part the input from the external sensors or the scoring of the severity of the subject's movement disorder or the movement disorder symptoms as input into a closed loop control system to deliver electrical stimulation or medication to lessen or relieve the symptoms of the disorder, or to appropriately treat the disorder in a non-symptomatic way. The treatment delivery system comprises the at least one external sensor having a signal for measuring a subject's external body motion or a physiological signal associated with a movement disorder. A treatment delivery system for electrical stimulation further comprises an implanted electrode which when activated sends an electrical stimulus to surrounding tissues such as a skeletal muscle or the subthalamic nucleus of the brain. The system further comprises a pulse generator which activates to send an electrical current to the implanted electrode based in part on a signal from the at least one external sensor. Similarly, a treatment delivery system for medicine further comprises a reservoir for some form of medication, preferably liquid, that can either be delivered to the subject internally or transcutaneously. The system further comprises an actuator or pump which when activated and deactivated allows the medication to be delivered from the reservoir to the subject. Finally, the system further comprises a closed-loop control system which activates and deactivates the actuator or pump based in part on a signal from the at least one external sensor.

Figure 13:
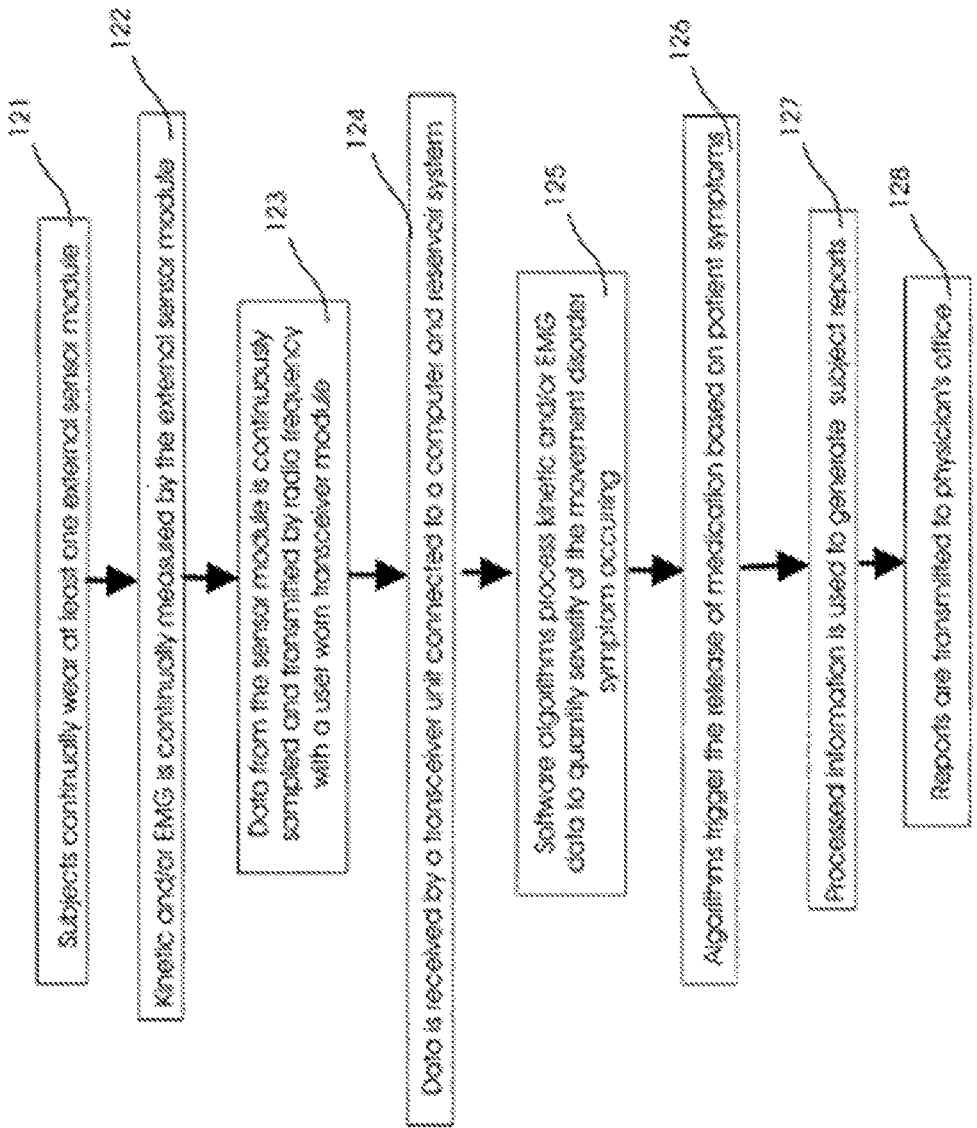
FIG. 13. Flow diagram for one embodiment of a closed-loop drug delivery system of the present invention.

FIG. 13 is a flow diagram for one embodiment of a closed-loop drug delivery system of the present invention. In this embodiment, the subjects continually wear at least one external sensor module 121. Kinetic motion and/or EMG is continually measured by the external sensor module 122. Data from the external sensor module is continuously sampled and transmitted by radio frequency with a subject worn transceiver module 123. The transmitted data is received by a transceiver unit connected to a reservoir system 124 with embedded processing. Software algorithms process kinetic and/or EMG data to quantify the severity of the movement disorder symptom occurring 124. The software algorithms trigger the release of medication based on the subject's symptoms 126, or the overall severity of the movement disorder 125. The processed information is then used to generate subject reports or data 127, and the reports or data are transmitted to technician, clinician or physician for review 128.

Figure 14:
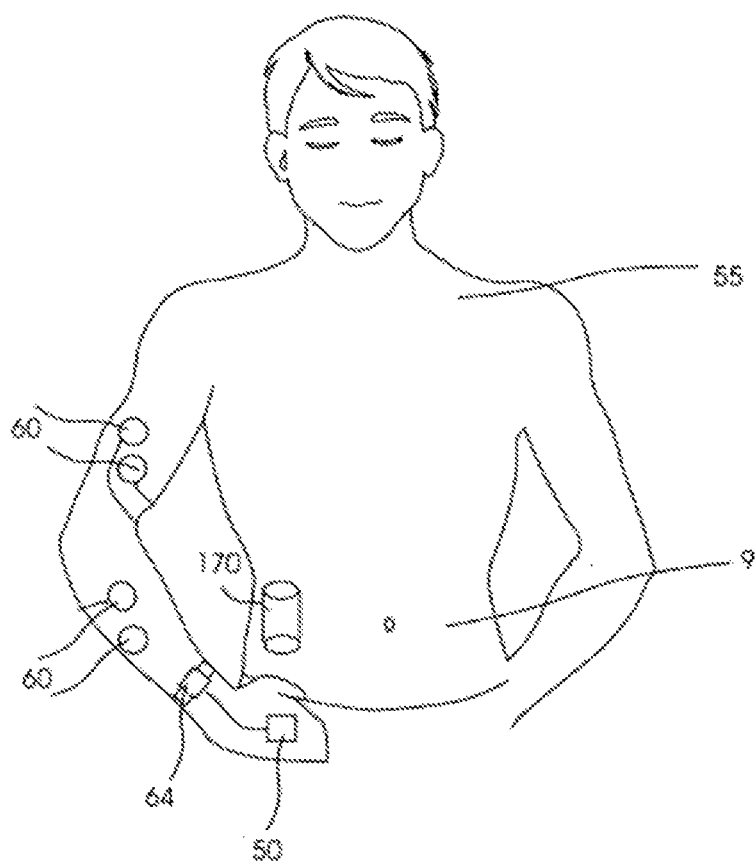
FIG. 14. Schematic showing placement of various components of closed loop drug delivery system with an implantable reservoir.

FIG. 14 is a schematic diagram showing placement of various components of closed loop drug delivery system with an implantable reservoir. In FIG. 14, the subject 55 is wearing a closed loop drug delivery system. The closed loop drug may have an external sensor module 50, a subject worn transceiver module 64, EMG electrodes 60, a reservoir 170 for holding medication with an embedded transceiver and processor and actuator for allowing delivery (not shown), and a controller for activating and deactivating the actuator based in part on the signal from the at least one of the sensor modules 50. In this example a reservoir 170 being implanted into the abdomen 9 of the subject. The reservoir 170 containing medication, which is released into the subject's body through activation of an actuator. The respective transceiver module 64 being connected to the EMG electrodes 60 and external sensor modules 50 via electrical pathways or wires (not shown). The transceiver module 64 being further being connected either wirelessly or via electrical pathways or wires (not shown) to a controller (not shown), which activates and deactivates an actuator (not shown) to release medication from the implantable reservoir 170.

Figure 15:
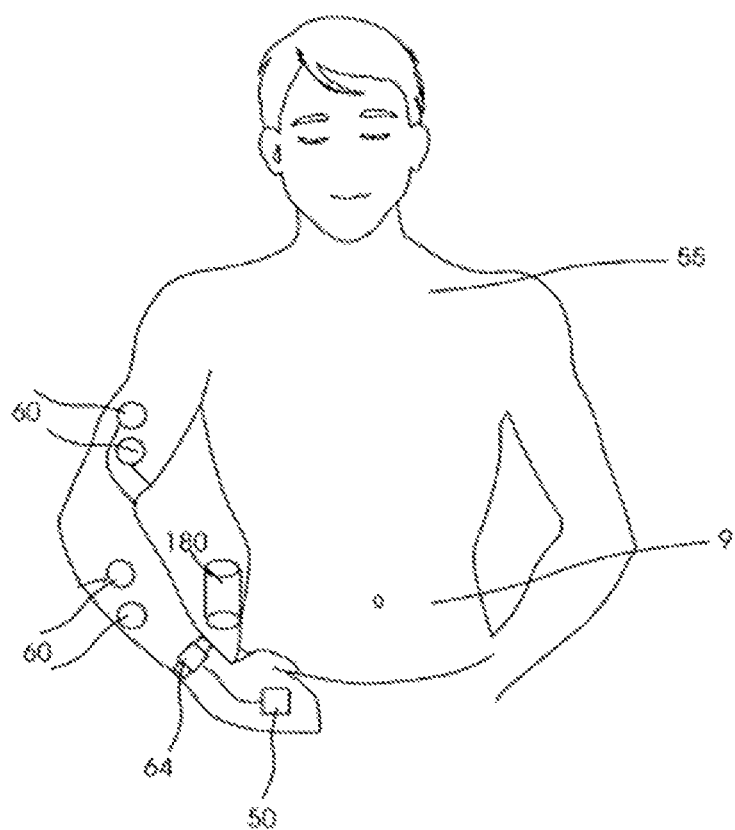
FIG. 15. Schematic showing placement of various components of closed loop drug delivery system with an external reservoir to transcutaneous delivery.

FIG. 15 is a schematic diagram showing placement of various components of a closed loop drug delivery system with an external reservoir to transcutaneous delivery. In FIG. 15, the subject 55 is wearing a closed loop drug delivery system. The closed loop drug delivery system may have an external sensor module 50, a subject worn transceiver module 64, EMG electrodes 60, a reservoir 180 for holding medication with an embedded transceiver and processor and actuator for allowing delivery (not shown), and a controller for activating and deactivating the actuator based in part on the signal from the at least one of the sensor modules 50. In this example a reservoir 180 is attached externally to the abdomen 9 of the subject. The reservoir 180 containing medication, which is released into the subject's body through activation of an actuator. The respective transceiver module 64 being connected to the EMG electrodes 60 and external sensor module 50 via electrical pathways or wires (not shown). The transceiver module 64 being further being connected either wirelessly or via electrical pathways or wires (not shown) to a controller (not shown), which activates and deactivates an actuator (not shown) to release medication from the implantable reservoir 180.

Figure 16:
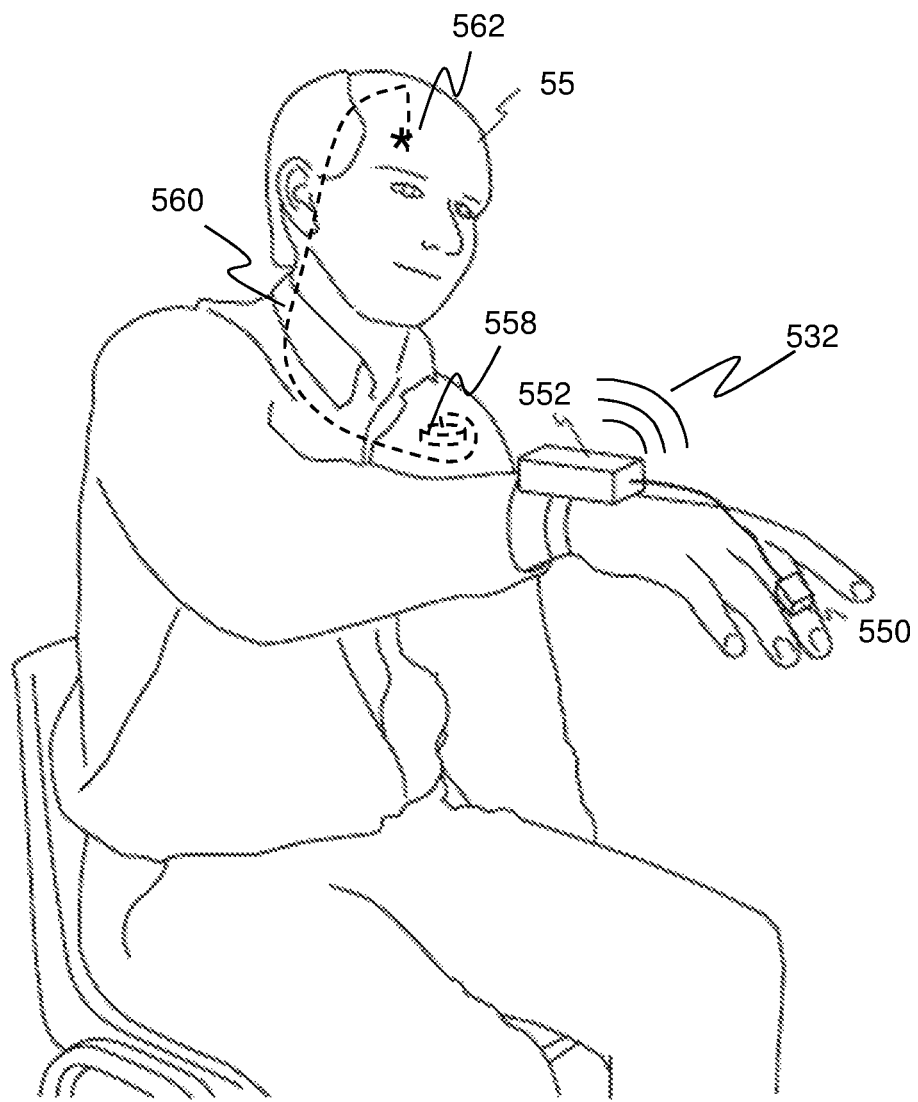
FIG. 16. Schematic showing closed-loop deep brain stimulation system.

FIG. 16 is a schematic showing a closed-loop deep brain stimulation (DBS) system. A movement measuring device, worn by a subject 55, and comprising a sensor module 550 and transceiver unit 552 continually measures the subject's movement data during while at home during activities of daily living and clinically directed tasks. The transceiver unit is capable of correlating with a central database 220 or database system through a wired or wireless communication system 532, such as the internet, Bluetooth, or the like, and using a trained algorithm to optimize a custom deep brain stimulation treatment protocol for the subject 216, 218. Such a protocol may include the amplitude (volts), current (amps), frequency (Hz), and pulse width (microseconds), or other parameters known to those skilled in the art. This protocol is then communicated to an implantable pulse generator 558 via the transceiver 552 or another external processing unit (not shown). When activated according to the protocol, the implantable pulse generator 558 sends an electronic pulse through an implanted wire and electrode lead 560 to generate a stimulus 562 in the subject's brain. After the treatment protocol is updated, the sensor module 550 continues to record new movement data and update treatment protocols as necessary according to the subject's change in symptom severity as in the embodiment described in FIG. 9B.

DBS units like those in the present embodiment may be powered by a rechargeable lithium-ion battery unit and can deliver stimulation to 1 or 2 leads which are generally implanted in the subthalamic nucleus, globus pallidus interna, or ventro intermediate nucleus of the thalamus. A typical implanted DBS stimulation lead consists of a thin insulated needle comprising four platinum/iridium electrodes spaced 0.5 or 1.5 mm apart along the length of the lead. One or multiple leads may be implanted in a target brain region or regions to provide symptom-inhibiting high-frequency stimulation, although some research suggests that excellent results can be achieved even when the lead is implanted distant from a target region. A DBS lead is connected to an implantable pulse generator (IPG), which serves as a controller and power source, via an extension cable tunneled subcutaneously to a subcutaneous pocket in the chest or abdominal cavity. The IPG typically includes the rechargeable lithium-ion battery and circuitry for telemetered communication with an external programming device used to adjust, or "tune," DBS lead stimulation parameters, which may include stimulation frequency, amplitude, pulse width (or wavelength), and contact configuration (that is, the selection of which electrodes are utilized from among the four electrodes available on a lead, and, if two or more electrodes are active, the relative polarity of each). These parameters are initially set during implantation surgery and are then further fined-tuned in the outpatient clinic or in a doctor's office following surgery to maximize therapeutic benefit and minimize undesirable stimulation-induced side effects. The first such tuning session usually takes place several weeks following implantation surgery, after the patient has recovered and inflammation at the lead placement site has subsided.

Initial DBS parameters are generally set for a pulse width of 60 microseconds and a frequency of 130 Hz. Voltage is then "turned on" and the amplitude incremented to a clinical level until subject symptoms begin to disappear. After an effective amplitude is found, the other parameters may also be tuned to further optimize the DBS settings. During the tuning process, the DBS unit allows pulse width to vary from 60 to 450 microseconds with a 10 microsecond resolution, however, typical values are usually kept between 60 and 120 microseconds. Frequency can be set from 2 to 250 Hz with a 5 Hz resolution, but generally only higher frequencies (over 100 Hz) show positive results, therefore general settings are usually between 130 and 185 Hz. Amplitude can range from 0 to 10.5 volts with a 0.05 volt resolution (the full range of amplitudes includes the negative values to account for both anodic and cathodic configurations of electrodes), however, the 1 to 3.5 V range is generally most acceptable (more specifically, 2.5-3.5 V for subjects with Parkinson's Disease). Additionally, in some embodiments, the DBS unit may be current controlled, meaning the amplitude of the stimulation is a current rather than a voltage. In these cases, the amplitude can range from 0 to 25.5 milliamps with a 0.1 mA resolution.

The components of the unit, including the battery and integrated circuits, are hermetically sealed within an oval-shaped titanium case in order to protect it from body fluids. The case can also have an external insulating coating to help minimize possible skeletal muscle stimulation at the implant site. One side of the unit, however, remains uninsulated so that it may serve as the positive electrode when using a unipolar configuration. The unit also contains octapolar in-line connectors for each electrode extension and multiple timers and counters. While a wireless device(s) is the preferred for the present system, the portable therapy system may also be a tethered system or a partially tethered partially wireless system.

Figure 17:
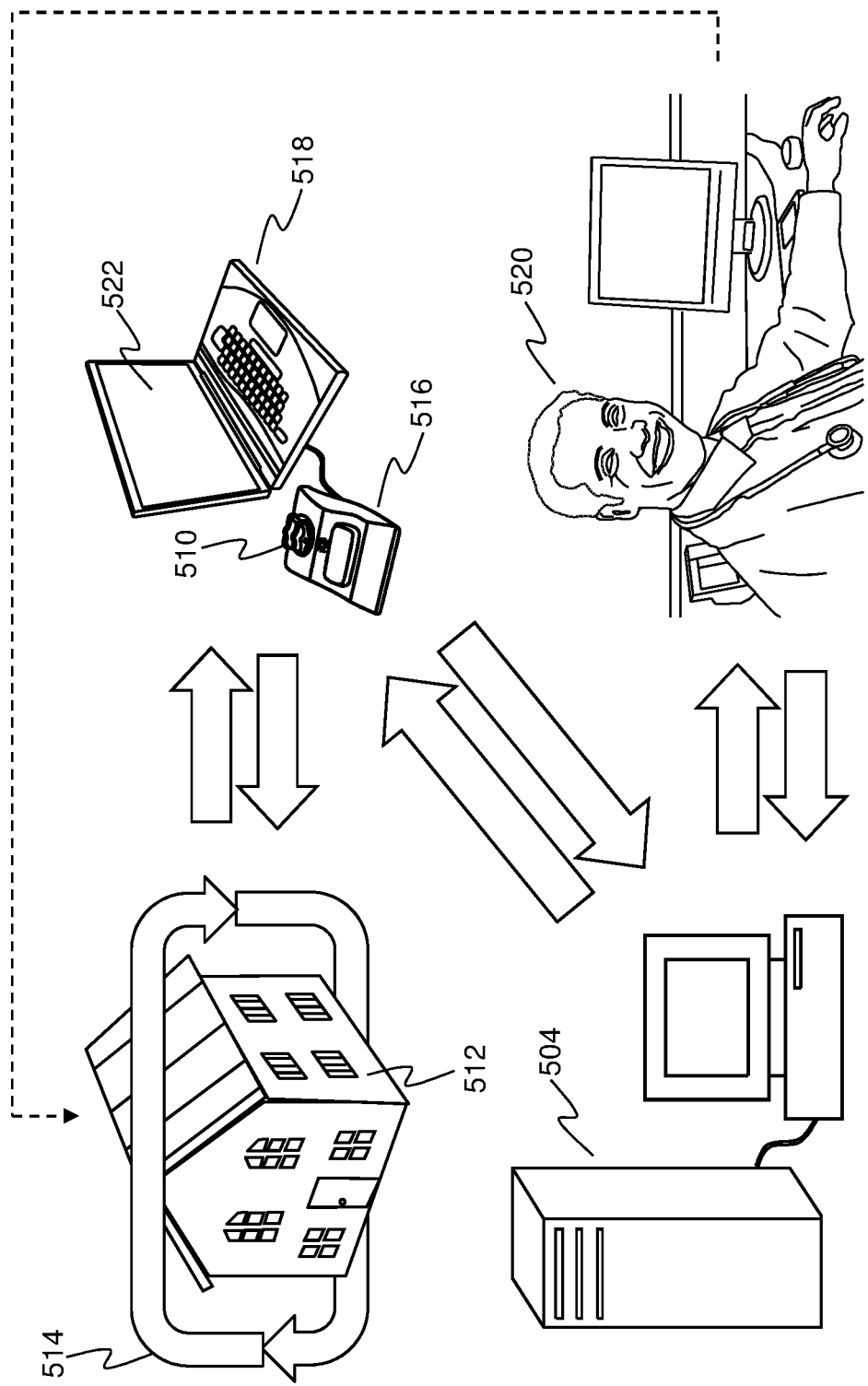
FIG. 17. Graphic depiction of continuous home movement recording and treatment tuning with the ability for remote clinician intervention.

FIG. 17 illustrates continuous home movement recording and treatment tuning with the ability for remote clinician intervention. A subject (not shown) inside the home 512 or at another location wears a movement measuring apparatus 510 while performing activities of daily living inside his home 512. While performing the activities, the movement measuring apparatus 510 continually records 514 the subject's movement data. The movement measuring apparatus 510 in this embodiment can then be docked at a docking station 516, which transfers the subject's recorded movement data 604 to a processor 518 via any wired or wireless connection known by those skilled in the art such as Bluetooth or USB. Using a trained algorithm, the processor 518 can correlate the subject's continuously recorded movement data with a central database 220 to determine a custom treatment. Once the processor 518 and central database 220 contain the subject's new customized treatment, a remote third party, such as a clinician 520, can be alerted to or retrieve the customized treatment from the central database 220 via the internet or other communication system. The clinician 520 may then intervene and prescribe a new treatment based on movement data scores from the central database 220. Additionally, the processor 518 may output the new recommended treatment on a screen 522 for the subject to see, who may then begin the new treatment without clinical intervention, or automatically program the subject's treatment device.

Figure 18:
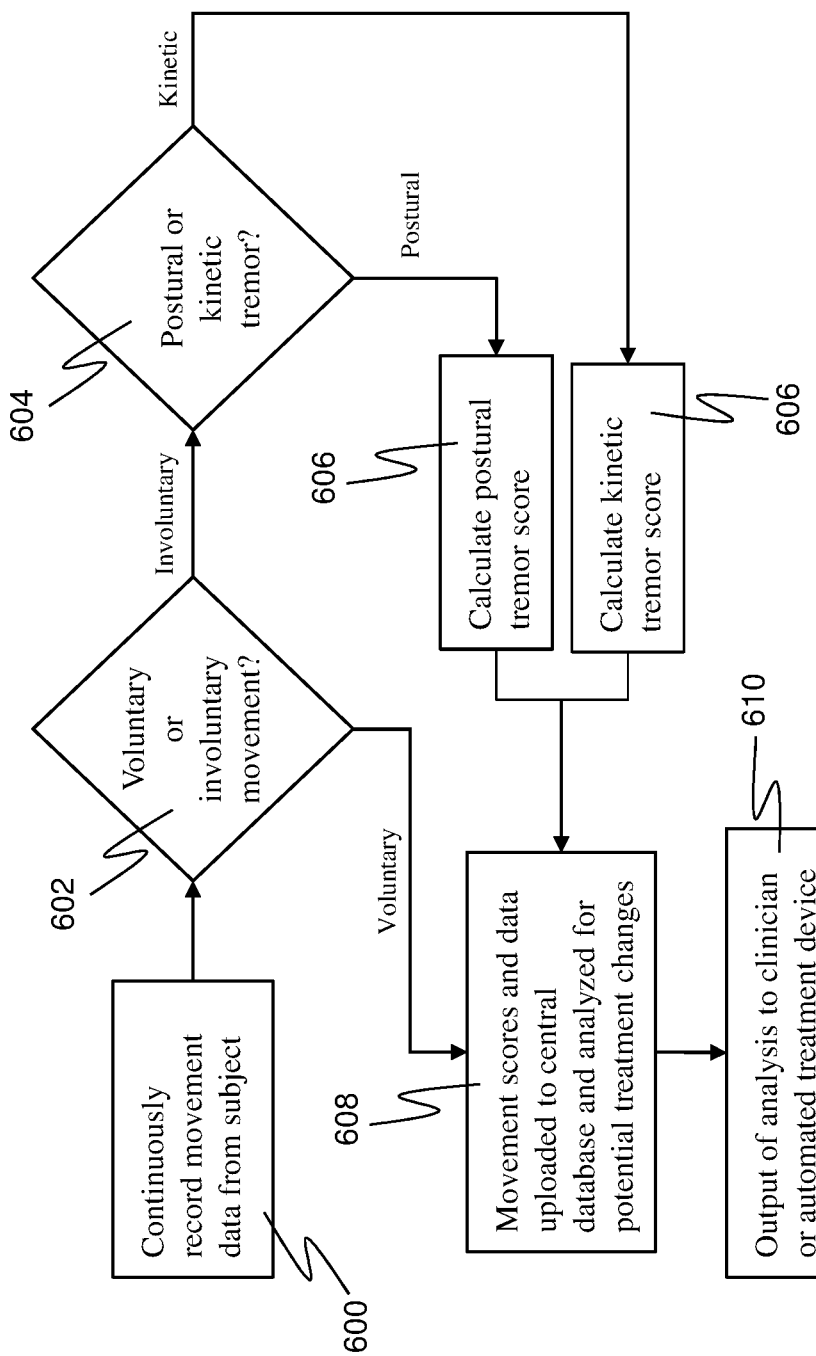
FIG. 18. Flow diagram for one embodiment of a trained algorithm to score and distinguish between movement disorder symptoms and activities of daily living.

FIG. 18 illustrates one embodiment of a trained algorithm that distinguishes and scores movement disorder symptoms such as tremor from activities of daily living or other voluntary movement. The trained algorithm used to distinguish and score movement disorder symptoms may comprise, for example, one or more of a simple or multiple linear regression, an artificial neural network, a Bayesian network, or a genetic algorithm. The output of the trained algorithm may be a single score or multiple scores of any scale; however, a single score on the same scale as that of the TRS (0-4) may be preferred in certain applications where simplicity or familiarity is the paramount concern, while more sophisticated scores and scales may be preferred for other advanced applications, such as those that involve recommendations for treatment or closed-loop automated treatment delivery. Scores determined by the trained algorithm may, for example, be used to generate physician reports, output alerts to the clinician and/or subject, update databases, training sets, and/or the like to aid in the training of other correlation and scoring algorithms, or automate new treatment protocols for medication delivery or electrical stimulation systems. Furthermore, scores are not simply meant to be a rescaling of a measured quantity. Rather, preferably they should be representative of a score that a skilled clinician might give to the subject during a movement analysis exam in the clinician's office using a standardized scale such as the UPDRS.

The trained algorithm of this embodiment is preferably trained using reference data, particularly where the data comprises clinician-assigned movement disorder test scores given on the tremor rating scale (TRS), and more particularly when the scores are given for tests from the TRS motor examination; however, any scale may be used so long as it remains consistent throughout training and use. This process is described in more detail in Heldman, et al., "Essential tremor quantification during activities of daily living," *Parkinsonism and Related Disorders*, Vol. 17, No. 7, pp. 537-542. August 2011, which is herein incorporated by reference. Reference data is preferably obtained using a training set generated by at least 10 adults with clinically diagnosed essential tremor and of varying ages (for example, 56-83 years old in one embodiment), disease durations (for example, 10-40 years in one embodiment), and tremor frequencies (for example, 4.2-9.6 Hz, with a mean of 6.1 Hz and a standard of 0.9 Hz in one embodiment). In the present embodiment, movement data is preferably recorded using a sensor unit on the subject's finger and comprising at least three axes each of accelerometers and gyroscopes. The subjects of the present embodiment are also video taped while performing each task. In this embodiment, each subject then performs a sequence of eleven tasks for approximately 15 seconds including seven based on the TRS (for example, having subjects place their hands in their laps, hold their arms extended horizontally, repeatedly reach out and touch their noses, pour water between two cups, drink water from a cup, use a spoon to drink water, and draw a spiral) and four tasks that resembled more routine activities of daily living but were not part of any standardized rating scale (for example, typing on a computer keyboard, using a computer mouse, folding laundry, and suing a remote control). This sequence of tasks is preferably repeated in this embodiment at least six times by each subject with a 3-5 minute rest period between each block of eleven tasks.

Preferably in this embodiment, videos of the subjects performing the TRS tasks are randomized and scored by four experienced movement disorder specialists who are blinded to subject identity. The raters preferably enter a 0-4 score for the present embodiment, according to the TRS, which are then averaged across the four raters to minimize variability. Next, the data is preferably bandpass filtered, from 0.1 to 3.0 Hz (voluntary band) and 4.0 to 12 Hz (tremor band). The magnitude of the logarithm of the peak power of the three orthogonal (x, y, and z) angular velocity signals is used to distinguish voluntary motion from involuntary motion 602 for a given data set. A person skilled in the art would understand the term "peak power" to mean the maximum value (in units of power) on a power spectrum derived by any means known in the art (e.g., FFT, wavelet transform, etc.) from a sample of data, in this case angular velocity as obtained from a gyroscope. If the movement is deemed involuntary, the algorithm next determines whether the tremor was postural or kinetic 604 using pre-determined thresholds based on a database or training set for the algorithm.

Thresholds for postural and kinetic tremor in this embodiment were determined based on the average logarithm of the peak power of the three orthogonal angular velocity signals for the known subjects of the previous training set performing TRS postural (rest, arms outstretched) and kinetic (nose-touching, pouring, drinking, spooning, spiral drawing) tasks. Two separate linear regression models were also derived from the recorded motion data and clinician scores of the seven TRS tasks, one each for the postural and kinetic tremor data and following the general structure of equation (1):

$$R = b_0 + B_a \cdot P_a + B_g \cdot P_g \tag{1}$$

where R is the average clinician rating, $P_a$ and $P_g$ are the processed peak powers of the accelerometer and gyroscope recordings as described above, and $B_a$, $B_g$, and $b_0$ are the regression coefficients. These two models were tested using a "one left out" technique. This meant a single regression was computed using all but one data point. The resulting regression model and coefficients were then used to compute an output score for the data point that was left out. The analysis was repeated leaving each data point out once. The coefficient of determination ($r^2$) and root-mean-square (RMS) error between regression model outputs and average clinician scores were computed for all generalization data.

The appropriate equation (1) model (postural or kinetic) is then chosen 604 based on the thresholds just described in order to calculate a TRS tremor score 606. Preferably, this calculated score 606 is representative of any TRS score given by a clinician, however, since they are calculated in the home and therefore outside of a clinical office, the scores are preferably uploaded to a central database 608 for the clinician to access. More preferably, this central database 220 is also used in conjunction with other algorithms to determine new treatment protocols based at least in part on the calculated TRS score 606 and automatically update a subject's treatment device as described in great detail earlier in this application.

It will be apparent to those skilled in the art that various modifications and variations can be made to the present invention or its various embodiments without departing from the spirit and scope of the invention. Thus, it is intended that the present invention cover the modifications and variations of this invention provided they come within the scope of the appended claims and their equivalents.

What is claimed:

1. A system for quantification and treatment of symptoms of a subject having a movement disorder, comprising:
    a movement measuring device adapted for continuously or intermittently acquiring movement data corresponding to movement of a subject during activities of daily living and/or while performing at least one directed task, the movement measuring apparatus comprising at least one sensor having a signal from which the movement data is acquired,
    at least one database comprising previous movement data from the subject and/or other subjects;
    a processor comprising at least one algorithm, the processor in communication electrically or wirelessly with the movement measuring device and with the at least one database, the at least one algorithm adapted to quantify a severity of at least one symptom of the subject's movement disorder over a period of time and to calculate a new recommended treatment protocol based at least in part on the movement data and the previous movement data, the processor further being in wireless radio frequency communication for receiving the movement data and/or transmitting the new recommended treatment protocol; and
    a treatment delivery device for receiving the new recommended treatment protocol calculated by the at least one algorithm and administering treatment, the treatment delivery device being programmable or reprogrammable based on a recommended treatment protocol.

2. The system of claim 1, wherein the treatment delivery device is a drug delivery device for providing pharmaceutical or medication therapy and comprises a drug reservoir for holding the drug or medication prior to administration to the subject and an actuator or pump for delivering the drug or medication from the reservoir to the subject.

3. The system of claim 2, wherein the previous movement data comprised in the at least one database includes one or more of movement data measured by the or another movement measuring device, movement disorder histories, treatment histories, and measured physiological signals.

4. The system of claim 2, wherein the at least one symptom quantified and treated by the system is dyskinesia, gait disturbances and balance disturbances, tremor or bradykinesia.

5. The system of claim 2, wherein the system is a closed-loop drug delivery system.

6. The system of claim 2, wherein the processor is further adapted to transmit the new recommended treatment protocol is to a clinician prior to the new recommended treatment protocol being entered into the treatment delivery device.

7. A system for real-time quantification of symptoms of a subject having a movement disorder, comprising:
    a movement measuring device adapted for continuously or intermittently acquiring movement data corresponding to movement of a subject during activities of daily living and/or while performing at least one directed task, the movement measuring device comprising at least one sensor having a signal from which the movement data is acquired,
    at least one database comprising previous movement data from the subject and/or other subjects;
    a processor comprising at least one algorithm, the processor adapted for being in communication with the movement measuring device and with the at least one database, the at least one algorithm adapted to quantify a severity of at least one symptom of the subject's movement disorder in real-time over a period of time and to calculate a new recommended treatment protocol based at least in part on the movement data and the previous movement data, the processor further being in wireless radio frequency communication for receiving the movement data and/or transmitting the new recommended treatment protocol; and
    a treatment delivery device for receiving the new recommended treatment protocol calculated by the at least one algorithm and administering treatment, the treatment delivery device being programmable or reprogrammable based on a recommended treatment protocol.

8. The system of claim 7, wherein the previous movement data comprised in the at least one database includes one or more of movement data measured by the or another movement measuring device, movement disorder histories, treatment histories, and measured physiological signals.

9. The system of claim 8, wherein the at least one symptom quantified and treated by the system is dyskinesia, gait and/or disturbances, tremor or bradykinesia.

10. The system of claim 9, wherein the quantification of severity of at least one symptom is based on one or more variables computed from the acquired movement data, the one or more variables including peak frequency, average amplitude, average power, frequency, peak frequency, number of hesitations, linear or exponential fit coefficients used to fit a model to the amplitude of a subject's movement over time, or range of motion.

11. The system of claim 10, wherein the treatment delivery device is a drug delivery device, and the recommended treatment protocol comprises one or more of a new drug to administer, a new drug dose, and dose timing.

12. The system of claim 7, wherein the system is a closed-loop drug delivery system.

13. The system of claim 7, wherein the processor is further adapted to transmit the new recommended treatment protocol to a clinician prior to the new recommended treatment protocol being entered into the treatment delivery device.

14. A system for quantification of symptoms of a subject having a movement disorder, comprising:
   a portable movement measuring device adapted for continuously or intermittently acquiring movement data corresponding to continuous movement of a subject during activities of daily living and/or while performing at least one directed task, the movement measuring device comprising at least one sensor having a signal from which the movement data is acquired;
   at least one database comprising previous movement data from the subject and/or other subjects;
   a processor comprising at least one algorithm, the processor in electrical or wireless communication with the movement measuring device and with the at least one database, the at least one algorithm adapted to quantify a severity of at least one symptom of the subject's movement disorder, the movement disorder having one or more of the symptoms from a group consisting of dyskinesia, gait disturbances and balance disturbances, bradykinesia, rigidity, rest tremor, postural tremor and kinetic tremor, the at least one algorithm further adapted to calculate a new recommended treatment protocol based at least in part on the movement data and the previous movement data, the processor further being in wireless radio frequency communication for receiving the movement data and/or transmitting the new recommended treatment protocol;
   an output or communications device adapted for outputting or otherwise communicating the quantification of the at least one symptom and/or the new recommended treatment protocol to a clinician, the subject or other user for review and analysis; and
   at least one radio frequency wireless interface between the movement disorder device and the processor for transmitting the movement data and/or the processor and the output or communications device for transmitting the quantification of the at least one symptom.

15. The system in claim 14, wherein the previous movement data comprised in the at least one database includes one or more of movement data measured by the or another movement measuring device, movement disorder histories, treatment histories, and measured physiological signals.

16. The system in claim 15, wherein the quantification of severity of at least one symptom is based on one or more variables computed from the acquired movement data, the one or more variables including peak frequency, average amplitude, average power, frequency, peak frequency, number of hesitations, linear or exponential fit coefficients used to fit a model to the amplitude of a subject's movement over time, or range of motion.

17. The system in claim 16, further comprising a treatment delivery device for receiving the new recommended treatment protocol calculated by the at least one algorithm and administering treatment, the treatment delivery device being programmable or reprogrammable based on a recommended treatment protocol, and the treatment delivery device is a drug delivery device, and the recommended treatment protocol comprises one or more of a new drug to administer, a new drug dose, and dose timing.

18. The system in claim 17, wherein a cell phone or computer comprises the processor.

19. The system of claim 17, wherein the system is a closed-loop drug delivery system.

20. The system of claim 17, wherein the processor is further adapted to transmit the new recommended treatment protocol to a clinician prior to the new recommended treatment protocol being entered into the treatment delivery device.

* * * * *